(12) United States Patent
Zhang et al.

(10) Patent No.: US 9,090,994 B2
(45) Date of Patent: Jul. 28, 2015

(54) ANTIBODY HUMANIZATION BY FRAMEWORK ASSEMBLY

(75) Inventors: Jianbing Zhang, Orleans (CA); Shu Wu, Nanjing (CN)

(73) Assignee: Nanjingjinsirui Science & Technology Biology Corp., Nanjing (CN)

( * ) Notice: Subject to any disclaimer, the term of this patent is extended or adjusted under 35 U.S.C. 154(b) by 0 days.

(21) Appl. No.: 13/492,264

(22) Filed: Jun. 8, 2012

(65) Prior Publication Data

US 2012/0316085 A1    Dec. 13, 2012

Related U.S. Application Data

(60) Provisional application No. 61/494,593, filed on Jun. 8, 2011.

(51) Int. Cl.
*C40B 30/04*    (2006.01)

(52) U.S. Cl.
CPC ..................................... *C40B 30/04* (2013.01)

(58) Field of Classification Search
None
See application file for complete search history.

(56) References Cited

PUBLICATIONS

Rader et al. (May 5, 2000) Journal of Biological Chemistry vol. 275 pp. 13668 to 13676.*
Knappik et al. (Feb. 11, 2000) Journal of Molecular Biology vol. 296 pp. 57 to 86.*

* cited by examiner

*Primary Examiner* — Christian Boesen
(74) *Attorney, Agent, or Firm* — Panitch Schwarze Belisario & Nadel LLP

(57) ABSTRACT

An improved method for producing humanized antibody or an antigen binding fragment thereof is described. The method, designated framework-assembly, bypasses the reliance on structural biology and the construction of large libraries. It is easier to implement and more efficient than the rational design and empirical methods. Also described are humanized antibodies produced by the method and related framework-assembly library.

12 Claims, 8 Drawing Sheets
(4 of 8 Drawing Sheet(s) Filed in Color)

A

VH-aM (SEQ ID NO: 5)

cagatccagttggtgcagtctggacctgagctgaagaagcctggagagacagtcaggatc
tcctgcaaggcttctgggtataccttcacaactgctggaatgcagtgggtgcaaaagatg
ccaggaaaggggtttgaagtggattggctggataaacacccactctggagtgccaaaatat
gcagaagacttcaagggacggtttgccttctctttggaaacctctgccagcactgcatat
ttacagatgaccaacctcaacaatgaggacacggctacgtatttctgtgcgagagggtat
ggtaaggggggggtattttgctatggactactggggtcaaggaacctcagtcaccgtctcc
tca

VL-aM (SEQ ID NO: 7)

gatgttgtgatgacccaaattccattctccctgcctgtcagtcttggagatcaagcctcc
atctcttgcagatctagtcagagccttgtacacagtaatggaaacacctatttacattgg
tacgtgcagaagccaggccagtctccaaagctcctgatctacaaagtttccaaccgattt
tctggggtcccagacaggttcagtggcagtggatcagggacatatttcacactcaagatc
agcagagtggaggctgaggatctgggagtttatttctgctctcaaagtacacgtgttccg
tggacgttcggtggaggcaccaagctggaaatcaaa

B

VH-aM (SEQ ID NO: 6)

```
1           11          21          31          41
QIQLVQSGPE  LKKPGETVRI  SCKASGYTFT  TAGMQWVQKM  PGKGLKWISW
 V                       C  CCVCV                      VVV
                            V  V 51 52 52A   61          71          81 82 82A 82C 91
INTHSGVPKY  AEDFKGRFAF  SLETSASTAY  LQMTNLNNED  TATYFCARGY
 V  V       C  V        V           S S 82B S               V C
    V                                                        V 101 100 100A 100C  121
GKGGYFAMDY  WGQGTSVTVS  S
 100B 100D
 S     F
```

VL-aM (SEQ ID NO: 8)

```
1           11          21  27 27A 27C 27D 27E  41
DVVMTQIPFS  LPVSLGDQAS  ISCRSSQSLV  HSNGNTYLHW  YVQKPGQSPK
 C V        S  S          RSSQSLV                V V S
 V                        27B 51          61          71          81          91
LLIYKVSNRF  SGVPDRFSGS  GSGTYFTLKI  SRVEAEDLGV  YFCSQSTRVP
V V C V                 C  V  V V S C                     S
    V                                           V
101         111
WTFGGGTKLE  IK
 V           F
```

A
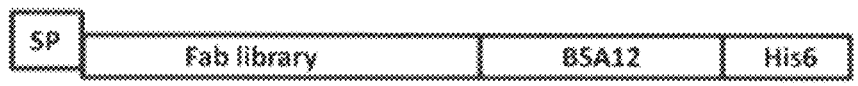
B
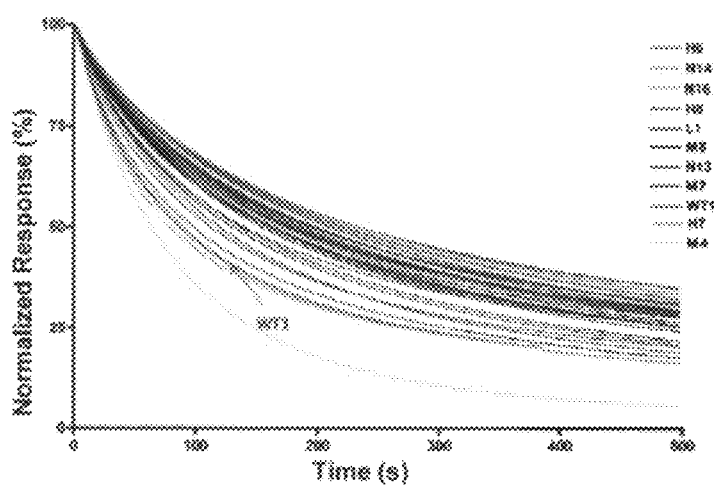
Figure 6.

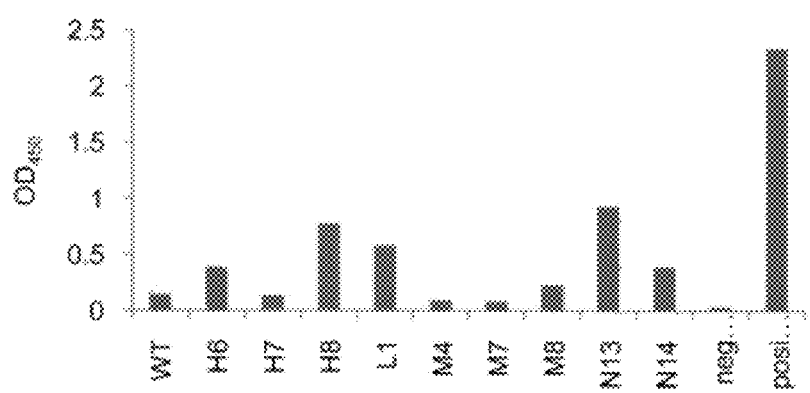
Figure 8. Humaness evaluation by ELSIA.

SEQUENCE LISTING

```
<160> NUMBER OF SEQ ID NOS: 68

<210> SEQ ID NO 1
<211> LENGTH: 24
<212> TYPE: DNA
<213> ORGANISM: Mus musculus

<400> SEQUENCE: 1
ttattactcg cggcccagcc ggcc                                          24

<210> SEQ ID NO 2
<211> LENGTH: 26
<212> TYPE: DNA
<213> ORGANISM: Mus musculus

<400> SEQUENCE: 2
ggtgcagcca ccgtacgttt gatttc                                        26

<210> SEQ ID NO 3
<211> LENGTH: 25
<212> TYPE: DNA
<213> ORGANISM: Mus musculus

<400> SEQUENCE: 3
catggccgag gtgcagctgg ctagc                                         25

<210> SEQ ID NO 4
<211> LENGTH: 25
<212> TYPE: DNA
<213> ORGANISM: Mus musculus

<400> SEQUENCE: 4
tgcggcccca tttgcggccg cagag                                         25

<210> SEQ ID NO 5
<211> LENGTH: 363
<212> TYPE: DNA
<213> ORGANISM: Mus musculus

<400> SEQUENCE: 5
cagatccagt tggtgcagtc tggacctgag ctgaagaagc ctggagagac agtcaggatc    60
tcctgcaagg cttctgggta taccttcaca actgctggaa tgcagtgggt gcaaaagatg   120
```

```
ccaggaaagg gtttgaagtg gattggctgg ataaacaccc actctggagt gccaaaatat    180
gcagaagact tcaagggacg gtttgccttc tctttggaaa cctctgccag cactgcatat    240
ttacagatga ccaacctcaa caatgaggac acggctacgt atttctgtgc gagagggtat    300
ggtaaggggg ggtattttgc tatggactac tggggtcaag aacctcagt caccgtctcc    360 tca                                                                  363
```

<210> SEQ ID NO 6
<211> LENGTH: 121
<212> TYPE: PRT
<213> ORGANISM: Mus musculus

<400> SEQUENCE: 6

```
Gln Ile Gln Leu Val Gln Ser Gly Pro Glu Leu Lys Lys Pro Gly Glu
1               5                   10                  15

Thr Val Arg Ile Ser Cys Lys Ala Ser Gly Tyr Thr Phe Thr Thr Ala
            20                  25                  30

Gly Met Gln Trp Val Gln Lys Met Pro Gly Lys Gly Leu Lys Trp Ile
        35                  40                  45

Gly Trp Ile Asn Thr His Ser Gly Val Pro Lys Tyr Ala Glu Asp Phe
    50                  55                  60

Lys Gly Arg Phe Ala Phe Ser Leu Glu Thr Ser Ala Ser Thr Ala Tyr
65                  70                  75                  80

Leu Gln Met Thr Asn Leu Asn Asn Glu Asp Thr Ala Thr Tyr Phe Cys
                85                  90                  95

Ala Arg Gly Tyr Gly Lys Gly Gly Tyr Phe Ala Met Asp Tyr Trp Gly
            100                 105                 110

Gln Gly Thr Ser Val Thr Val Ser Ser
        115                 120
```

<210> SEQ ID NO 7
<211> LENGTH: 336
<212> TYPE: DNA
<213> ORGANISM: Mus musculus

<400> SEQUENCE: 7

```
gatgttgtga tgacccaaat tccattctcc ctgcctgtca gtcttggaga tcaagcctcc    60
atctcttgca gatctagtca gagccttgta cacagtaatg aaacaccta tttacattgg   120 tacgtgcaga agccaggcca gtctccaaag ctcctgatct acaaagtttc caaccgattt   180
tctggggtcc cagacaggtt cagtggcagt ggatcaggga catatttcac actcaagatc   240
agcagagtgg aggctgagga tctgggagtt tatttctgct ctcaaagtac acgtgttccg   300
tggacgttcg gtggaggcac caagctggaa atcaaa                             336
```

<210> SEQ ID NO 8
<211> LENGTH: 112
<212> TYPE: PRT
<213> ORGANISM: Mus musculus

<400> SEQUENCE: 8

```
Asp Val Val Met Thr Gln Ile Pro Phe Ser Leu Pro Val Ser Leu Gly
1               5                   10                  15

Asp Gln Ala Ser Ile Ser Cys Arg Ser Ser Gln Ser Leu Val His Ser
            20                  25                  30

Asn Gly Asn Thr Tyr Leu His Trp Tyr Val Gln Lys Pro Gly Gln Ser
        35                  40                  45
```

```
Pro Lys Leu Leu Ile Tyr Lys Val Ser Asn Arg Phe Ser Gly Val Pro
        50                  55                  60

Asp Arg Phe Ser Gly Ser Gly Ser Gly Thr Tyr Phe Thr Leu Lys Ile
 65                  70                  75                  80

Ser Arg Val Glu Ala Glu Asp Leu Gly Val Tyr Phe Cys Ser Gln Ser
                 85                  90                  95

Thr Arg Val Pro Trp Thr Phe Gly Gly Gly Thr Lys Leu Glu Ile Lys
                100                 105                 110
```

<210> SEQ ID NO 9
<211> LENGTH: 25
<212> TYPE: PRT
<213> ORGANISM: Homo sapiens

<400> SEQUENCE: 9

```
Gln Val Gln Leu Val Gln Ser Gly His Glu Val Lys Asn Pro Gly Ala
 1               5                  10                  15

Ser Val Lys Val Ser Cys Lys Ala Ser
                20                  25
```

<210> SEQ ID NO 10
<211> LENGTH: 25
<212> TYPE: PRT
<213> ORGANISM: Homo sapiens

<400> SEQUENCE: 10

```
Gln Val Gln Leu Val Gln Ser Gly Ser Glu Leu Lys Lys Pro Gly Ala
 1               5                  10                  15

Ser Val Lys Val Ser Cys Lys Ala Ser
                20                  25
```

<210> SEQ ID NO 11
<211> LENGTH: 14
<212> TYPE: PRT
<213> ORGANISM: Homo sapiens

<400> SEQUENCE: 11

```
Trp Val Pro Gln Ala Pro Gly Gln Gly Leu Glu Trp Met Gly
 1               5                  10
```

<210> SEQ ID NO 12
<211> LENGTH: 14
<212> TYPE: PRT
<213> ORGANISM: Homo sapiens

<400> SEQUENCE: 12

```
Trp Val Arg Gln Ala Pro Gly Gln Gly Leu Glu Trp Met Gly
 1               5                  10
```

<210> SEQ ID NO 13
<211> LENGTH: 30
<212> TYPE: PRT
<213> ORGANISM: Homo sapiens

<400> SEQUENCE: 13

```
Arg Phe Val Phe Ser Leu Asp Thr Ser Val Ser Thr Ala Tyr Leu Gln
 1               5                  10                  15

Ile Cys Ser Leu Lys Ala Glu Asp Thr Ala Val Tyr Tyr Cys
                20                  25                  30
```

<210> SEQ ID NO 14
<211> LENGTH: 30

<212> TYPE: PRT
<213> ORGANISM: Homo sapiens

<400> SEQUENCE: 14

Arg Phe Val Phe Ser Leu Asp Thr Ser Val Ser Thr Ala Tyr Leu Gln
1               5                   10                  15

Ile Ser Ser Leu Lys Ala Glu Asp Thr Ala Val Tyr Tyr Cys
            20                  25                  30

<210> SEQ ID NO 15
<211> LENGTH: 30
<212> TYPE: PRT
<213> ORGANISM: Homo sapiens

<400> SEQUENCE: 15

Arg Phe Val Phe Ser Leu Asp Thr Ser Val Ser Thr Ala Tyr Leu Gln
1               5                   10                  15

Ile Ser Thr Leu Lys Ala Glu Asp Thr Ala Val Tyr Tyr Cys
            20                  25                  30

<210> SEQ ID NO 16
<211> LENGTH: 30
<212> TYPE: PRT
<213> ORGANISM: Homo sapiens

<400> SEQUENCE: 16

Arg Phe Val Phe Ser Met Asp Thr Ser Ala Ser Thr Ala Tyr Leu Gln
1               5                   10                  15

Ile Ser Ser Leu Lys Ala Glu Asp Met Ala Met Tyr Tyr Cys
            20                  25                  30

<210> SEQ ID NO 17
<211> LENGTH: 11
<212> TYPE: PRT
<213> ORGANISM: Homo sapiens

<400> SEQUENCE: 17

Trp Gly Gln Gly Thr Thr Val Thr Val Ser Ser
1               5                   10

<210> SEQ ID NO 18
<211> LENGTH: 23
<212> TYPE: PRT
<213> ORGANISM: Homo sapiens

<400> SEQUENCE: 18

Asp Ile Val Met Thr Gln His Leu Leu Ser Leu Pro Ile Pro Leu Gly
1               5                   10                  15

Glu Pro Ala Ser Ile Ser Cys
            20

<210> SEQ ID NO 19
<211> LENGTH: 23
<212> TYPE: PRT
<213> ORGANISM: Homo sapiens

<400> SEQUENCE: 19

Asp Ile Val Met Thr Gln Ser Pro Leu Ser Leu Pro Val Thr Pro Gly
1               5                   10                  15

Glu Pro Ala Ser Ile Ser Cys
            20

```
<210> SEQ ID NO 20
<211> LENGTH: 23
<212> TYPE: PRT
<213> ORGANISM: Homo sapiens

<400> SEQUENCE: 20

Asp Ile Val Met Thr Gln Thr Pro Leu Ser Leu Pro Val Thr Pro Gly
1               5                   10                  15

Glu Pro Ala Ser Ile Ser Cys
            20

<210> SEQ ID NO 21
<211> LENGTH: 23
<212> TYPE: PRT
<213> ORGANISM: Homo sapiens

<400> SEQUENCE: 21

Asp Ile Val Met Thr Gln Thr Pro Leu Ser Leu Ser Val Thr Pro Gly
1               5                   10                  15

Gln Pro Ala Ser Ile Ser Cys
            20

<210> SEQ ID NO 22
<211> LENGTH: 23
<212> TYPE: PRT
<213> ORGANISM: Homo sapiens

<400> SEQUENCE: 22

Asp Ile Val Met Thr Gln Thr Pro Leu Ser Ser Pro Val Thr Leu Gly
1               5                   10                  15

Gln Pro Ala Ser Ile Ser Cys
            20

<210> SEQ ID NO 23
<211> LENGTH: 23
<212> TYPE: PRT
<213> ORGANISM: Homo sapiens

<400> SEQUENCE: 23

Asp Ile Val Met Thr Gln Thr Pro Leu Ser Ser Pro Val Thr Leu Gly
1               5                   10                  15

Gln Pro Ala Ser Ile Ser Phe
            20

<210> SEQ ID NO 24
<211> LENGTH: 23
<212> TYPE: PRT
<213> ORGANISM: Homo sapiens

<400> SEQUENCE: 24

Asp Ile Val Met Thr Gln Thr Pro Pro Ser Leu Pro Val Asn Pro Gly
1               5                   10                  15

Glu Pro Ala Ser Ile Ser Cys
            20

<210> SEQ ID NO 25
<211> LENGTH: 23
<212> TYPE: PRT
<213> ORGANISM: Homo sapiens

<400> SEQUENCE: 25

Asp Val Val Met Thr Gln Ser Pro Leu Ser Leu Pro Val Thr Leu Gly
1               5                   10                  15
```

Gln Pro Ala Ser Ile Ser Cys
            20

<210> SEQ ID NO 26
<211> LENGTH: 23
<212> TYPE: PRT
<213> ORGANISM: Homo sapiens

<400> SEQUENCE: 26

Glu Ile Val Met Thr Gln Thr Pro Leu Ser Leu Ser Ile Thr Pro Gly
1               5                   10                  15

Glu Gln Ala Ser Ile Ser Cys
            20

<210> SEQ ID NO 27
<211> LENGTH: 23
<212> TYPE: PRT
<213> ORGANISM: Homo sapiens

<400> SEQUENCE: 27

Glu Ile Val Met Thr Gln Thr Pro Leu Ser Leu Ser Ile Thr Pro Gly
1               5                   10                  15

Glu Gln Ala Ser Met Ser Cys
            20

<210> SEQ ID NO 28
<211> LENGTH: 15
<212> TYPE: PRT
<213> ORGANISM: Homo sapiens

<400> SEQUENCE: 28

Trp Phe Leu Gln Lys Ala Arg Pro Val Ser Thr Leu Leu Ile Cys
1               5                   10                  15

<210> SEQ ID NO 29
<211> LENGTH: 15
<212> TYPE: PRT
<213> ORGANISM: Homo sapiens

<400> SEQUENCE: 29

Trp Phe Leu Gln Lys Ala Arg Pro Val Ser Thr Leu Leu Ile Tyr
1               5                   10                  15

<210> SEQ ID NO 30
<211> LENGTH: 15
<212> TYPE: PRT
<213> ORGANISM: Homo sapiens

<400> SEQUENCE: 30

Trp Phe Gln Gln Arg Pro Gly Gln Ser Pro Arg Arg Leu Ile Tyr
1               5                   10                  15

<210> SEQ ID NO 31
<211> LENGTH: 15
<212> TYPE: PRT
<213> ORGANISM: Homo sapiens

<400> SEQUENCE: 31

Trp Leu Gln Gln Arg Pro Gly Gln Pro Pro Arg Leu Leu Ile Tyr
1               5                   10                  15

<210> SEQ ID NO 32
<211> LENGTH: 15

```
<212> TYPE: PRT
<213> ORGANISM: Homo sapiens

<400> SEQUENCE: 32

Trp Tyr Leu Gln Lys Pro Gly Gln Pro Pro Gln Leu Leu Ile Tyr
1               5                   10                  15

<210> SEQ ID NO 33
<211> LENGTH: 15
<212> TYPE: PRT
<213> ORGANISM: Homo sapiens

<400> SEQUENCE: 33

Trp Tyr Leu Gln Lys Pro Gly Gln Ser Pro Gln Leu Leu Ile Tyr
1               5                   10                  15

<210> SEQ ID NO 34
<211> LENGTH: 15
<212> TYPE: PRT
<213> ORGANISM: Homo sapiens

<400> SEQUENCE: 34

Trp Tyr Pro Gln Lys Pro Gly Gln Ser Pro Gln Leu Leu Ile Tyr
1               5                   10                  15

<210> SEQ ID NO 35
<211> LENGTH: 32
<212> TYPE: PRT
<213> ORGANISM: Homo sapiens

<400> SEQUENCE: 35

Gly Val Pro Asp Arg Phe Ser Gly Ser Gly Ala Gly Thr Asp Phe Thr
1               5                   10                  15

Leu Lys Ile Ser Arg Val Glu Ala Glu Asp Val Gly Val Tyr Tyr Cys
                20                  25                  30

<210> SEQ ID NO 36
<211> LENGTH: 32
<212> TYPE: PRT
<213> ORGANISM: Homo sapiens

<400> SEQUENCE: 36

Gly Val Pro Asp Arg Phe Ser Gly Ser Gly Ser Gly Ser Asp Phe Thr
1               5                   10                  15

Leu Lys Ile Ser Trp Val Glu Ala Glu Asp Val Gly Val Tyr Tyr Cys
                20                  25                  30

<210> SEQ ID NO 37
<211> LENGTH: 32
<212> TYPE: PRT
<213> ORGANISM: Homo sapiens

<400> SEQUENCE: 37

Gly Val Pro Asp Arg Phe Ser Gly Ser Gly Ser Gly Thr Asp Phe Thr
1               5                   10                  15

Leu Lys Ile Ser Arg Val Glu Ala Glu Asp Phe Gly Val Tyr Tyr Cys
                20                  25                  30

<210> SEQ ID NO 38
<211> LENGTH: 32
<212> TYPE: PRT
<213> ORGANISM: Homo sapiens

<400> SEQUENCE: 38
```

Gly Val Pro Asp Arg Phe Ser Gly Ser Gly Thr Asp Phe Thr
1               5                   10                  15

Leu Lys Ile Ser Arg Val Glu Ala Glu Asp Val Gly Val Tyr Tyr Cys
            20                  25                  30

<210> SEQ ID NO 39
<211> LENGTH: 32
<212> TYPE: PRT
<213> ORGANISM: Homo sapiens

<400> SEQUENCE: 39

Gly Val Pro Asn Lys Phe Ser Gly Ser Arg Ser Gly Thr Gly Phe Thr
1               5                   10                  15

Leu Lys Phe Ser Lys Val Glu Ala Glu Asp Val Gly Val Tyr Cys Cys
            20                  25                  30

<210> SEQ ID NO 40
<211> LENGTH: 9
<212> TYPE: PRT
<213> ORGANISM: Homo sapiens

<400> SEQUENCE: 40

Gly Gly Gly Thr Lys Val Glu Ile Lys
1               5

<210> SEQ ID NO 41
<211> LENGTH: 121
<212> TYPE: PRT
<213> ORGANISM: Mus musculus

<400> SEQUENCE: 41

Gln Ile Gln Leu Val Gln Ser Gly Pro Glu Leu Lys Lys Pro Gly Glu
1               5                   10                  15

Thr Val Arg Ile Ser Cys Lys Ala Ser Gly Tyr Thr Phe Thr Thr Ala
            20                  25                  30

Gly Met Gln Trp Val Gln Lys Met Pro Gly Lys Gly Leu Lys Trp Ile
        35                  40                  45

Gly Trp Ile Asn Thr His Ser Gly Val Pro Lys Tyr Ala Glu Asp Phe
    50                  55                  60

Lys Gly Arg Phe Ala Phe Ser Leu Glu Thr Ser Ala Ser Thr Ala Tyr
65                  70                  75                  80

Leu Gln Ile Ser Asn Leu Lys Asn Glu Asp Thr Ala Thr Tyr Phe Cys
                85                  90                  95

Ala Arg Gly Tyr Gly Lys Gly Gly Tyr Tyr Ala Met Asp Tyr Trp Gly
            100                 105                 110

Gln Gly Thr Ser Val Thr Val Ser Ser
        115                 120

<210> SEQ ID NO 42
<211> LENGTH: 121
<212> TYPE: PRT
<213> ORGANISM: Homo sapiens

<400> SEQUENCE: 42

Gln Val Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr Ser Tyr
            20                  25                  30

Ala Met Asn Trp Val Arg Gln Ala Pro Gly Gln Gly Leu Glu Trp Met

```
                35                  40                  45
Gly Trp Ile Asn Thr Asn Thr Gly Asn Pro Thr Tyr Ala Gln Gly Phe
         50                  55                  60

Thr Gly Arg Phe Val Phe Ser Leu Asp Thr Ser Val Ser Thr Ala Tyr
 65                  70                  75                  80

Leu Gln Ile Ser Ser Leu Lys Ala Glu Asp Thr Ala Val Tyr Tyr Cys
                 85                  90                  95

Ala Arg Gly Tyr Gly Lys Gly Tyr Tyr Gly Met Asp Val Trp Gly
             100                 105                 110

Gln Gly Thr Thr Val Thr Val Ser Ser
             115                 120

<210> SEQ ID NO 43
<211> LENGTH: 121
<212> TYPE: PRT
<213> ORGANISM: Artificial Sequence
<220> FEATURE:
<223> OTHER INFORMATION: Graft

<400> SEQUENCE: 43

Gln Val Gln Leu Val Gln Ser Gly Ser Glu Leu Lys Lys Pro Gly Ala
  1               5                  10                  15

Ser Val Lys Val Ser Cys Lys Ala Ser Gly Tyr Thr Phe Thr Thr Ala
                 20                  25                  30

Gly Met Gln Trp Val Arg Gln Ala Pro Gly Gln Gly Leu Glu Trp Met
             35                  40                  45

Gly Trp Ile Asn Thr His Ser Gly Val Pro Lys Tyr Ala Glu Asp Phe
         50                  55                  60

Lys Gly Arg Phe Val Phe Ser Leu Asp Thr Ser Val Ser Thr Ala Tyr
 65                  70                  75                  80

Leu Gln Ile Ser Ser Leu Lys Ala Glu Asp Thr Ala Val Tyr Tyr Cys
                 85                  90                  95

Ala Arg Gly Tyr Gly Lys Gly Tyr Phe Ala Met Asp Tyr Trp Gly
             100                 105                 110

Gln Gly Thr Thr Val Thr Val Ser Ser
             115                 120

<210> SEQ ID NO 44
<211> LENGTH: 112
<212> TYPE: PRT
<213> ORGANISM: Mus musculus

<400> SEQUENCE: 44

Asp Val Val Met Thr Gln Ile Pro Phe Ser Leu Pro Val Ser Leu Gly
  1               5                  10                  15

Asp Gln Ala Ser Ile Ser Cys Arg Ser Ser Gln Ser Leu Val His Ser
                 20                  25                  30

Asn Gly Asn Thr Tyr Leu His Trp Tyr Val Gln Lys Pro Gly Gln Ser
             35                  40                  45

Pro Lys Leu Leu Ile Tyr Lys Val Ser Asn Arg Phe Ser Gly Val Pro
         50                  55                  60

Asp Arg Phe Ser Gly Ser Gly Ser Gly Thr Tyr Phe Thr Leu Lys Ile
 65                  70                  75                  80

Ser Arg Val Glu Ala Glu Asp Leu Gly Val Tyr Phe Cys Ser Gln Ser
                 85                  90                  95

Thr Arg Val Pro Trp Thr Phe Gly Gly Gly Thr Lys Leu Glu Ile Lys
             100                 105                 110
```

```
<210> SEQ ID NO 45
<211> LENGTH: 112
<212> TYPE: PRT
<213> ORGANISM: Mus musculus

<400> SEQUENCE: 45

Asp Val Val Met Thr Gln Ile Pro Phe Ser Leu Pro Val Ser Leu Gly
1               5                   10                  15

Asp Gln Ala Ser Ile Ser Cys Arg Ser Ser Gln Ser Leu Val His Ser
            20                  25                  30

Asn Gly Asn Thr Tyr Leu His Trp Tyr Val Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Tyr Phe Thr Leu Lys Ile
65                  70                  75                  80

Ser Arg Val Glu Ala Glu Asp Leu Gly Val Tyr Phe Cys Ser Gln Ser
                85                  90                  95

Thr Arg Val Pro Trp Thr Phe Gly Gly Gly Thr Lys Leu Glu Ile Lys
            100                 105                 110

<210> SEQ ID NO 46
<211> LENGTH: 112
<212> TYPE: PRT
<213> ORGANISM: Mus musculus

<400> SEQUENCE: 46

Asp Val Val Met Thr Gln Ile Pro Phe Ser Leu Pro Val Ser Leu Gly
1               5                   10                  15

Asp Gln Ala Ser Ile Ser Cys Arg Ser Ser Gln Ser Leu Val His Ser
            20                  25                  30

Asn Gly Asn Thr Tyr Leu His Trp Tyr Val Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Tyr Phe Thr Leu Lys Ile
65                  70                  75                  80

Ser Arg Val Glu Ala Glu Asp Leu Gly Val Tyr Phe Cys Ser Gln Ser
                85                  90                  95

Thr Arg Val Pro Trp Thr Phe Gly Gly Gly Thr Lys Leu Glu Ile Lys
            100                 105                 110

<210> SEQ ID NO 47
<211> LENGTH: 112
<212> TYPE: PRT
<213> ORGANISM: Mus musculus

<400> SEQUENCE: 47

Asp Val Val Met Thr Gln Thr Pro Leu Ser Leu Pro Val Ser Leu Gly
1               5                   10                  15

Asp Gln Ala Ser Ile Ser Cys Arg Ser Ser Gln Ser Leu Val His Ser
            20                  25                  30

Asn Gly Asn Thr Tyr Leu His Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60
```

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Phe Cys Ser Gln Ser
                85                  90                  95

Thr His Val Pro Trp Thr Phe Gly Gly Gly Thr Lys Leu Glu Ile Lys
            100                 105                 110

<210> SEQ ID NO 48
<211> LENGTH: 112
<212> TYPE: PRT
<213> ORGANISM: Homo sapiens

<400> SEQUENCE: 48

Asp Val Val Met Thr Gln Ser Pro Leu Ser Leu Pro Val Thr Leu Gly
1               5                   10                  15

Gln Pro Ala Ser Ile Ser Cys Arg Ser Ser Gln Ser Leu Val His Ser
            20                  25                  30

Asp Gly Asn Thr Tyr Leu Asn Trp Phe Gln Gln Arg Pro Gly Gln Ser
        35                  40                  45

Pro Arg Arg Leu Ile Tyr Lys Val Ser Asn Arg Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Gly
                85                  90                  95

Thr His Trp Pro Leu Thr Phe Gly Gly Gly Thr Lys Val Glu Ile Lys
            100                 105                 110

<210> SEQ ID NO 49
<211> LENGTH: 112
<212> TYPE: PRT
<213> ORGANISM: Artificial Sequence
<220> FEATURE:
<223> OTHER INFORMATION: Graft

<400> SEQUENCE: 49

Asp Val Val Met Thr Gln Ser Pro Leu Ser Leu Pro Val Thr Leu Gly
1               5                   10                  15

Gln Pro Ala Ser Ile Ser Cys Arg Ser Ser Gln Ser Leu Val His Ser
            20                  25                  30

Asn Gly Asn Thr Tyr Leu His Trp Phe Gln Gln Arg Pro Gly Gln Ser
        35                  40                  45

Pro Arg Arg Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Ser
                85                  90                  95

Thr Arg Val Pro Trp Thr Phe Gly Gly Gly Thr Lys Val Glu Ile Lys
            100                 105                 110

<210> SEQ ID NO 50
<211> LENGTH: 121
<212> TYPE: PRT
<213> ORGANISM: Homo sapiens

<400> SEQUENCE: 50

Gln Val Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr Ser Tyr
            20                  25                  30

Ala Met Asn Trp Val Arg Gln Ala Pro Gly Gln Gly Leu Glu Trp Met
        35                  40                  45

Gly Trp Ile Asn Thr Asn Thr Gly Asn Pro Thr Tyr Ala Gln Gly Phe
    50                  55                  60

Thr Gly Arg Phe Val Phe Ser Leu Asp Thr Ser Val Ser Thr Ala Tyr
65                  70                  75                  80

Leu Gln Ile Ser Ser Leu Lys Ala Glu Asp Thr Ala Val Tyr Tyr Cys
                85                  90                  95

Ala Arg Gly Tyr Gly Lys Gly Tyr Phe Ala Met Asp Tyr Trp Gly
            100                 105                 110

Gln Gly Thr Ser Val Thr Val Ser Ser
        115                 120

<210> SEQ ID NO 51
<211> LENGTH: 121
<212> TYPE: PRT
<213> ORGANISM: Homo sapiens

<400> SEQUENCE: 51

Gln Val Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr Ser Tyr
            20                  25                  30

Ala Met Asn Trp Val Arg Gln Ala Pro Gly Gln Gly Leu Glu Trp Met
        35                  40                  45

Gly Trp Ile Asn Thr Asn Thr Gly Asn Pro Thr Tyr Ala Gln Gly Phe
    50                  55                  60

Thr Gly Arg Phe Val Phe Ser Leu Asp Thr Ser Val Ser Thr Ala Tyr
65                  70                  75                  80

Leu Gln Ile Cys Ser Leu Lys Ala Glu Asp Thr Ala Val Tyr Tyr Cys
                85                  90                  95

Ala Arg Gly Tyr Gly Lys Gly Tyr Phe Ala Met Asp Tyr Trp Gly
            100                 105                 110

Gln Gly Thr Ser Val Thr Val Ser Ser
        115                 120

<210> SEQ ID NO 52
<211> LENGTH: 121
<212> TYPE: PRT
<213> ORGANISM: Homo sapiens

<400> SEQUENCE: 52

Gln Val Gln Leu Val Gln Ser Gly His Glu Val Lys Gln Pro Gly Ala
1               5                   10                  15

Ser Val Lys Val Ser Cys Lys Ala Ser Gly Tyr Ser Phe Thr Thr Tyr
            20                  25                  30

Gly Met Asn Trp Val Pro Gln Ala Pro Gly Gln Gly Leu Glu Trp Met
        35                  40                  45

Gly Trp Phe Asn Thr Tyr Thr Gly Asn Pro Thr Tyr Ala Gln Gly Phe
    50                  55                  60

Thr Gly Arg Phe Val Phe Ser Met Asp Thr Ser Ala Ser Thr Ala Tyr
65                  70                  75                  80

Leu Gln Ile Ser Ser Leu Lys Ala Glu Asp Met Ala Met Tyr Tyr Cys
                85                  90                  95

```
Ala Arg Gly Tyr Gly Lys Gly Tyr Phe Ala Met Asp Tyr Trp Gly
            100                 105                 110

Gln Gly Thr Ser Val Thr Val Ser Ser
        115                 120
```

<210> SEQ ID NO 53
<211> LENGTH: 121
<212> TYPE: PRT
<213> ORGANISM: Homo sapiens

<400> SEQUENCE: 53

```
Gln Val Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr Thr Ala
            20                  25                  30

Gly Met Gln Trp Val Arg Gln Ala Pro Gly Gln Gly Leu Glu Trp Met
        35                  40                  45

Gly Trp Ile Asn Thr His Ser Gly Val Pro Lys Tyr Ala Glu Asp Phe
    50                  55                  60

Lys Gly Arg Phe Val Phe Ser Leu Asp Thr Ser Val Ser Thr Ala Tyr
65                  70                  75                  80

Leu Gln Ile Ser Thr Leu Lys Ala Glu Asp Thr Ala Val Tyr Tyr Cys
                85                  90                  95

Ala Arg Gly Tyr Gly Lys Gly Tyr Phe Ala Met Asp Tyr Trp Gly
            100                 105                 110

Gln Gly Thr Ser Val Thr Val Ser Ser
        115                 120
```

<210> SEQ ID NO 54
<211> LENGTH: 112
<212> TYPE: PRT
<213> ORGANISM: Homo sapiens

<400> SEQUENCE: 54

```
Asp Val Val Met Thr Gln Ser Pro Leu Ser Leu Pro Val Thr Leu Gly
1               5                   10                  15

Gln Pro Ala Ser Ile Ser Cys Arg Ser Ser Gln Ser Leu Val His Ser
            20                  25                  30

Asp Gly Asn Thr Tyr Leu Asn Trp Phe Gln Gln Arg Pro Gly Gln Ser
        35                  40                  45

Pro Arg Arg Leu Ile Tyr Lys Val Ser Asn Arg Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Gly
                85                  90                  95

Thr His Trp Pro Trp Thr Phe Gly Gly Gly Thr Lys Val Glu Ile Lys
            100                 105                 110
```

<210> SEQ ID NO 55
<211> LENGTH: 112
<212> TYPE: PRT
<213> ORGANISM: Homo sapiens

<400> SEQUENCE: 55

```
Asp Ile Val Met Thr Gln Thr Pro Leu Ser Leu Ser Val Thr Pro Gly
1               5                   10                  15
```

```
Gln Pro Ala Ser Ile Ser Cys Lys Ser Ser Gln Ser Leu Leu His Ser
            20                  25                  30

Asp Gly Lys Thr Tyr Leu Tyr Trp Tyr Leu Gln Lys Pro Gly Gln Ser
        35                  40                  45

Pro Gln Leu Leu Ile Tyr Glu Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ser
                85                  90                  95

Thr Ile Gln Leu Trp Thr Phe Gly Gly Gly Thr Lys Val Glu Ile Lys
            100                 105                 110
```

<210> SEQ ID NO 56
<211> LENGTH: 112
<212> TYPE: PRT
<213> ORGANISM: Homo sapiens

<400> SEQUENCE: 56

```
Asp Val Val Met Thr Gln Ser Pro Leu Ser Leu Pro Val Thr Leu Gly
1               5                   10                  15

Gln Pro Ala Ser Ile Ser Cys Arg Ser Ser Gln Ser Leu Val Tyr Ser
            20                  25                  30

Asp Gly Asn Thr Tyr Leu Asn Trp Phe Gln Gln Arg Pro Gly Gln Ser
        35                  40                  45

Pro Arg Arg Leu Ile Tyr Lys Val Ser Asn Arg Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Gly
                85                  90                  95

Thr His Trp Pro Trp Thr Phe Gly Gly Gly Thr Lys Val Glu Ile Lys
            100                 105                 110
```

<210> SEQ ID NO 57
<211> LENGTH: 112
<212> TYPE: PRT
<213> ORGANISM: Homo sapiens

<400> SEQUENCE: 57

```
Asp Ile Val Met Thr Gln Thr Pro Leu Ser Leu Ser Val Thr Pro Gly
1               5                   10                  15

Gln Pro Ala Ser Ile Ser Cys Lys Ser Ser Gln Ser Leu Leu His Ser
            20                  25                  30

Asp Gly Lys Thr Tyr Leu Tyr Trp Tyr Leu Gln Lys Pro Gly Gln Ser
        35                  40                  45

Pro Gln Leu Leu Ile Tyr Glu Val Ser Ser Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Gly
                85                  90                  95

Ile His Leu Pro Trp Thr Phe Gly Gly Gly Thr Lys Val Glu Ile Lys
            100                 105                 110
```

<210> SEQ ID NO 58
<211> LENGTH: 112

```
<212> TYPE: PRT
<213> ORGANISM: Homo sapiens

<400> SEQUENCE: 58

Asp Ile Val Met Thr Gln Thr Pro Leu Ser Leu Ser Val Thr Pro Gly
1               5                   10                  15

Gln Pro Ala Ser Ile Ser Cys Lys Ser Ser Gln Ser Leu Leu His Ser
            20                  25                  30

Asp Gly Lys Thr Tyr Leu Tyr Trp Tyr Leu Gln Lys Pro Gly Gln Ser
        35                  40                  45

Pro Gln Leu Leu Ile Tyr Glu Val Ser Ser Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Gly
                85                  90                  95

Ile His Leu Pro Trp Thr Phe Gly Gly Gly Thr Lys Val Glu Ile Lys
            100                 105                 110

<210> SEQ ID NO 59
<211> LENGTH: 112
<212> TYPE: PRT
<213> ORGANISM: Homo sapiens

<400> SEQUENCE: 59

Asp Ile Val Met Thr Gln Thr Pro Leu Ser Pro Val Thr Leu Gly
1               5                   10                  15

Gln Pro Ala Ser Ile Ser Cys Arg Ser Ser Gln Ser Leu Val His Ser
            20                  25                  30

Asp Gly Asn Thr Tyr Leu Ser Trp Leu Gln Gln Arg Pro Gly Gln Pro
        35                  40                  45

Pro Arg Leu Leu Ile Tyr Lys Ile Ser Asn Arg Phe Ser Gly Val Pro
    50                  55                  60

Asp Arg Phe Ser Gly Ser Gly Ala Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Thr Gln Phe Pro Trp Thr Phe Gly Gly Gly Thr Lys Val Glu Ile Lys
            100                 105                 110

<210> SEQ ID NO 60
<211> LENGTH: 112
<212> TYPE: PRT
<213> ORGANISM: Homo sapiens

<400> SEQUENCE: 60

Asp Ile Val Met Thr Gln Thr Pro Leu Ser Leu Ser Val Thr Pro Gly
1               5                   10                  15

Gln Pro Ala Ser Ile Ser Cys Lys Ser Ser Gln Ser Leu Leu His Ser
            20                  25                  30

Asp Gly Lys Thr Tyr Leu Tyr Trp Tyr Leu Gln Lys Pro Gly Gln Pro
        35                  40                  45

Pro Gln Leu Leu Ile Tyr Glu Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ser
```

```
                    85                  90                  95

Ile Gln Leu Pro Trp Thr Phe Gly Gly Gly Thr Lys Val Glu Ile Lys
            100                 105                 110

<210> SEQ ID NO 61
<211> LENGTH: 112
<212> TYPE: PRT
<213> ORGANISM: Homo sapiens

<400> SEQUENCE: 61

Asp Val Val Met Thr Gln Ser Pro Leu Ser Leu Pro Val Thr Leu Gly
1               5                   10                  15

Gln Pro Ala Ser Ile Ser Cys Arg Ser Ser Gln Ser Leu Val Tyr Ser
            20                  25                  30

Asp Gly Asn Thr Tyr Leu Asn Trp Phe Gln Gln Arg Pro Gly Gln Ser
        35                  40                  45

Pro Arg Arg Leu Ile Tyr Lys Val Ser Asn Trp Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Gly
                85                  90                  95

Thr His Trp Pro Trp Thr Phe Gly Gly Gly Thr Lys Val Glu Ile Lys
            100                 105                 110

<210> SEQ ID NO 62
<211> LENGTH: 112
<212> TYPE: PRT
<213> ORGANISM: Homo sapiens

<400> SEQUENCE: 62

Asp Ile Val Met Thr Gln Thr Pro Leu Ser Ser Pro Val Thr Leu Gly
1               5                   10                  15

Gln Pro Ala Ser Ile Ser Phe Arg Ser Ser Gln Ser Leu Val His Ser
            20                  25                  30

Asp Gly Asn Thr Tyr Leu Ser Trp Leu Gln Gln Arg Pro Gly Gln Pro
        35                  40                  45

Pro Arg Leu Leu Ile Tyr Lys Val Ser Asn Arg Phe Ser Gly Val Pro
    50                  55                  60

Asp Arg Phe Ser Gly Ser Gly Ala Gly Thr Asp Phe Thr Leu Lys Ile
65                  70                  75                  80

Ser Arg Val Glu Ala Glu Asp Val Gly Val Tyr Tyr Cys Thr Gln Ala
                85                  90                  95

Thr Gln Phe Pro Trp Thr Phe Gly Gly Gly Thr Lys Val Glu Ile Lys
            100                 105                 110

<210> SEQ ID NO 63
<211> LENGTH: 112
<212> TYPE: PRT
<213> ORGANISM: Homo sapiens

<400> SEQUENCE: 63

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Tyr Asn Tyr Leu Asp Trp Tyr Leu Gln Lys Pro Gly Gln Ser
        35                  40                  45
```

-continued

Pro Gln Leu Leu Ile Tyr Leu Gly Ser Asn Arg Ala Ser Gly Val Pro
        50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Leu Gln Thr Pro Trp Thr Phe Gly Gly Gly Thr Lys Val Glu Ile Lys
            100                 105                 110

<210> SEQ ID NO 64
<211> LENGTH: 112
<212> TYPE: PRT
<213> ORGANISM: Homo sapiens

<400> SEQUENCE: 64

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
                20                  25                  30

Asn Gly Tyr Asn Tyr Leu Asp Trp Tyr Leu Gln Lys Pro Gly Gln Ser
            35                  40                  45

Pro Gln Leu Leu Ile Tyr Leu Gly Ser Asn Arg Ala Ser Gly Val Pro
        50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Leu Gln Thr Pro Trp Thr Phe Gly Gly Gly Thr Lys Val Glu Ile Lys
            100                 105                 110

<210> SEQ ID NO 65
<211> LENGTH: 113
<212> TYPE: PRT
<213> ORGANISM: Homo sapiens

<400> SEQUENCE: 65

Asp Ile Val Met Thr Gln Thr Pro Leu Ser Leu Pro Val Thr Pro Gly
1               5                   10                  15

Glu Pro Ala Ser Ile Ser Cys Arg Ser Ser Gln Ser Leu Leu Asp Ser
                20                  25                  30

Asp Asp Gly Asn Thr Tyr Leu Asp Trp Tyr Leu Gln Lys Pro Gly Gln
            35                  40                  45

Ser Pro Gln Leu Leu Ile Tyr Thr Leu Ser Tyr Arg Ala Ser Gly Val
        50                  55                  60

Pro Asp Arg Phe Ser Gly Ser Gly Ser Gly Thr Asp Phe Thr Leu Lys
65                  70                  75                  80

Ile Ser Arg Val Glu Ala Glu Asp Val Gly Val Tyr Tyr Cys Met Gln
                85                  90                  95

Arg Ile Glu Phe Pro Trp Thr Phe Gly Gly Gly Thr Lys Val Glu Ile
            100                 105                 110

Lys

```
<210> SEQ ID NO 66
<211> LENGTH: 113
<212> TYPE: PRT
<213> ORGANISM: Homo sapiens

<400> SEQUENCE: 66

Asp Ile Val Met Thr Gln Thr Pro Leu Ser Leu Pro Val Thr Pro Gly
1               5                   10                  15

Glu Pro Ala Ser Ile Ser Cys Arg Ser Ser Gln Ser Leu Leu Asp Ser
            20                  25                  30

Asp Asp Gly Asn Thr Tyr Leu Asp Trp Tyr Leu Gln Lys Pro Gly Gln
        35                  40                  45

Ser Pro Gln Leu Leu Ile Tyr Thr Leu Ser Tyr Arg Ala Ser Gly Val
    50                  55                  60

Pro Asp Arg Phe Ser Gly Ser Gly Ser Gly Thr Asp Phe Thr Leu Lys
65                  70                  75                  80

Ile Ser Arg Val Glu Ala Glu Asp Val Gly Val Tyr Tyr Cys Met Gln
                85                  90                  95

Arg Ile Glu Phe Pro Trp Thr Phe Gly Gly Gly Thr Lys Val Glu Ile
            100                 105                 110

Lys

<210> SEQ ID NO 67
<211> LENGTH: 112
<212> TYPE: PRT
<213> ORGANISM: Homo sapiens

<400> SEQUENCE: 67

Glu Ile Val Met Thr Gln Thr Pro Leu Ser Leu Ser Ile Thr Pro Gly
1               5                   10                  15

Glu Gln Ala Ser Ile Ser Cys Arg Ser Ser Gln Ser Leu Leu His Ser
            20                  25                  30

Asp Gly Tyr Thr Tyr Leu Tyr Trp Phe Leu Gln Lys Ala Arg Pro Val
        35                  40                  45

Ser Thr Leu Leu Ile Tyr Glu Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Phe Gly Val Tyr Tyr Cys Met Gln Asp
                85                  90                  95

Ala Gln Asp Pro Trp Thr Phe Gly Gly Gly Thr Lys Val Glu Ile Lys
            100                 105                 110

<210> SEQ ID NO 68
<211> LENGTH: 112
<212> TYPE: PRT
<213> ORGANISM: Homo sapiens

<400> SEQUENCE: 68

Glu Ile Val Met Thr Gln Thr Pro Leu Ser Leu Ser Ile Thr Pro Gly
1               5                   10                  15

Glu Gln Ala Ser Met Ser Cys Arg Ser Ser Gln Ser Leu Leu His Ser
            20                  25                  30

Asp Gly Tyr Thr Tyr Leu Tyr Trp Phe Leu Gln Lys Ala Arg Pro Val
        35                  40                  45

Ser Thr Leu Leu Ile Cys Glu Val Ser Asn Arg Phe Ser Gly Val Pro
    50                  55                  60
```

```
Asp Arg Phe Ser Gly Ser Gly Ser Gly Thr Asp Phe Thr Leu Lys Ile
65                  70                  75                  80

Ser Arg Val Glu Ala Glu Asp Phe Gly Val Tyr Tyr Cys Met Gln Asp
                85                  90                  95

Ala Gln Asp Pro Trp Thr Phe Gly Gly Gly Thr Lys Val Glu Ile Lys
                100                 105                 110
```

ANTIBODY HUMANIZATION BY FRAMEWORK ASSEMBLY

CROSS-REFERENCE TO RELATED APPLICATIONS

This application claims the benefit under 35 U.S.C. §119 (e) of U.S. Provisional Application No. 61/494,593, filed Jun. 8, 2011, the entire disclosure of which is hereby incorporated herein by reference.

FIELD OF INVENTION

This invention relates to methods and compositions of recombinant antibodies, in particular, humanized antibodies.

BACKGROUND OF THE INVENTION

Since the establishment of the hybridoma technology (1), a vast repertoire of murine monoclonal antibodies (mAbs) have been generated and characterized. Many of them have been applied in diagnosis of human diseases, such as cancers, infectious diseases, autoimmune diseases, etc. Their clinical use in the treatment of diseases, however, is limited mainly because the murine mAbs elicit human anti-murine antibodies (HAMA) responses in patients (2). The HAMA response occurred in up to 50% of patients upon administration of murine hybridoma-derived antibodies (3) and this has severely compromised the safety, efficacy, and biological half-life of these reagents. In addition, murine antibody constant regions are inefficient in directing suitable human immune effector functions for therapeutic effects. Efforts to produce human antibodies by hybridoma technology (4) and Epstein-Barr virus (EBV)-mediated B-lymphocyte transformation (5) have met with limited success. Their widespread application is hampered by the lack of robust human hybridoma fusion partners and the instability of EBV-transformed clones, respectively (6). As a means of circumventing the limitations of non-human mAbs and human antibodies, several strategies have been developed to convert non-human antibody sequences into human antibody sequences, a process termed antibody humanization, to exploit the non-human mAbs against a variety of human disease targets and turn them into effective therapeutic reagents.

Two major approaches have been used to transform murine antibodies into humanized antibodies: rational design and empirical methods. The rational design methods are characterized by antibody structural modeling, generating a few variants of the engineered antibodies and assessing their binding or any other property of interest. If the designed variants do not produce the expected results, a new cycle of design and binding assessment is initiated. The rational design methods include, but are not limited to, complementarity determining region (CDR) grafting, resurfacing, super-humanization and human string content optimization, among which, CDR grafting is the most widely used. Humanized antibody generated by CDR-grafting contains amino acids from the six CDRs of the parental murine mAb, which are grafted onto a human antibody framework. The low content of non-human sequence in humanized antibodies (~5%) has proven effective in both reducing the immunogenicity and prolonging the serum half-life in humans (7).

Unfortunately, simple grafting of CDR sequences often yields humanized antibodies that bind antigen much more weakly than the parental murine mAb, and decreases in affinity of up to several hundred-fold have been reported (Eigenbrot et al., 1994, *Proteins* 18, 49-62). To restore high affinity, the antibody must be further engineered to fine tune the structure of the antigen-binding loops. This is usually achieved by replacing key residues in the framework regions of the antibody variable domains with the matching sequence from the parental murine antibody. These framework residues are usually involved in supporting the conformation of the CDR loops, although some framework residues may themselves directly contact the antigen (Mian et al., 1991, *J Mol Biol* 217, 133-151). It has become apparent that the accomplishment of antibody humanization by rational method faces relatively high uncertainty. Moreover, broad application of this technology has also been restricted due to reliance on structural biology, which is not readily available for many laboratories.

In contrast to the rational design methods, empirical methods do not require the structure information of the antibody. They depend on the generation of large combinatorial libraries and selection of the desired variants by enrichment technologies such as phage, ribosome or yeast display, or by high throughput screening techniques. These methods rest on selection rather than making assumptions on the impact of mutations on the antibody structure. These methods include, but are not limited to, framework libraries, guided selection, framework shuffling and humaneering. However, the success of these methods relies mainly on the construction of large libraries, because high affinity antibodies can be isolated from the large size of antibody repertoires.

Antibody humanization is the core technology in antibody drug development. Although the first humanized antibody was generated decades ago, antibody humanization still faces many technology challenges.

There is a need of an improved method for antibody humanization. The present invention relates to such a method as well as humanized antibodies made by such a method.

BRIEF SUMMARY OF THE INVENTION

In one general aspect, embodiments of the present invention relate to a novel antibody humanization method that bypasses the reliance on structural biology and the construction of large libraries. The approach presented in this invention is more efficient in generating humanized antibodies than those in the prior art.

In one general aspect, the present invention relates to a method of producing a humanized antibody or an antigen binding fragment thereof for a non-human antibody to an antigen, comprising:

(1) constructing a heavy chain variable domain (VH) framework (FR) library comprising nucleic acids encoding a diversity of VHs, each of the VHs comprising FR1, FR2, FR3 and FR4 independently selected from corresponding FRs of a first number of homologous human germline VHs, and corresponding complementarity determining regions (CDRs) of the VH of the non-human antibody;

(2) constructing a light chain variable domain (VL) FR library comprising nucleic acids encoding a diversity of VLs, each of the VLs comprising FR1, FR2, FR3 and FR4 independently selected from corresponding FRs of a second number of homologous human germline VLs, and corresponding CDRs of the VL of the non-human antibody;

(3) constructing a framework-assembly library comprising nucleic acids encoding a diversity of Fabs or fragments thereof, each of the Fabs or the fragments thereof comprising a VH encoded by a nucleic acid in the VH FR library and a VL encoded by a nucleic acid in the VL FR library;

(4) expressing the framework-assembly library in host cells;

(5) identifying from the expressed framework-assembly library an Fab or a fragment thereof that binds to the antigen;

(6) identifying the VH and VL in the identified Fab or the fragment thereof as a humanized VH and a humanized VL, respectively, for the humanized antibody or the antigen binding fragment thereof; and (7) producing the humanized antibody or the antigen binding fragment thereof comprising the identified humanized VH and the humanized VL.

Other general aspects of the present invention relate to the humanized antibody or the antigen binding fragment thereof produced by a method according to an embodiment of the present invention, as well as compositions and methods of using the antibody or fragments thereof.

In another general aspect, the present invention relates to a framework-assembly library for a non-human antibody to an antigen. The library comprises nucleic acids encoding a diversity of Fabs or fragments thereof, each of the Fabs or the fragments thereof comprising a VH and a VL, wherein the VH comprises framework 1 (FR1), FR2, FR3 and FR4 independently selected from corresponding FRs of a first number of homologous human germline VHs and corresponding complementarity determining regions (CDRs) of the VH of the non-human antibody, and the VL comprises FR1, FR2, FR3 and FR4 independently selected from the corresponding FRs of a second number of homologous human germline VLs and corresponding CDRs of the VL of the non-human antibody According to an embodiment of the present invention, the framework-assembly library is expressed and the Fab or fragment thereof that binds to the antigen are selected by phage-display, preferably with two or more rounds of selection.

In a preferred embodiment of the present invention, more than one Fabs or fragments thereof that bind to the antigen are identified. The method further comprises measuring expression level of each of the more than one Fabs or fragments thereof in an expression cell, and identifying the VH and VL within the Fab or fragment thereof that has the highest expression level as the humanized VH and the humanized VL, respectively.

In another preferred embodiment of the present invention, more than one Fab or fragments thereof that bind to the antigen are identified, and the method further comprises measuring expression level of each of the more than one Fabs or fragments thereof in an expression cell, measuring the binding affinity of each of the more than one Fabs or fragments thereof to the antigen, and identifying the VH and VL within the Fab or fragment thereof that has a high expression level and a strong binding affinity as the humanized VH and the humanized VL, respectively.

In a preferred embodiment, the expression level of each of the more than one Fabs or fragments thereof is measured using an FASEBA (Fast Screen for Expression, Biophysical-properties and Affinity) system.

In an embodiment of the present invention, the non-human antibody is a rodent antibody, preferably a murine antibody.

Other aspects, features and advantages of the invention will be apparent from the following disclosure, including the detailed description of the invention and its preferred embodiments and the appended claims.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The foregoing summary, as well as the following detailed description of the invention, will be better understood when read in conjunction with the appended drawings. For the purpose of illustrating the invention, there are shown in the drawings embodiments which are presently preferred. It should be understood, however, that the invention is not limited to the precise arrangements and instrumentalities shown.

In the drawings:

Figure 3:
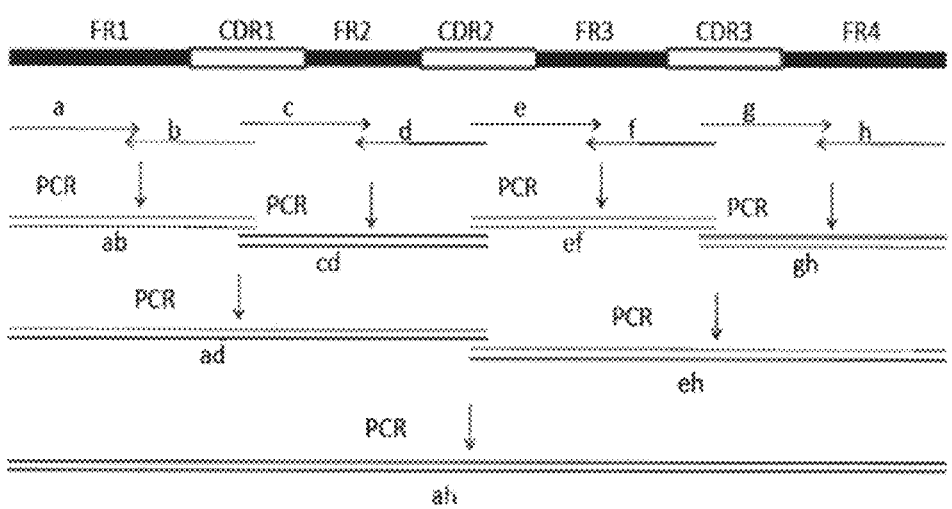
Figure 4:
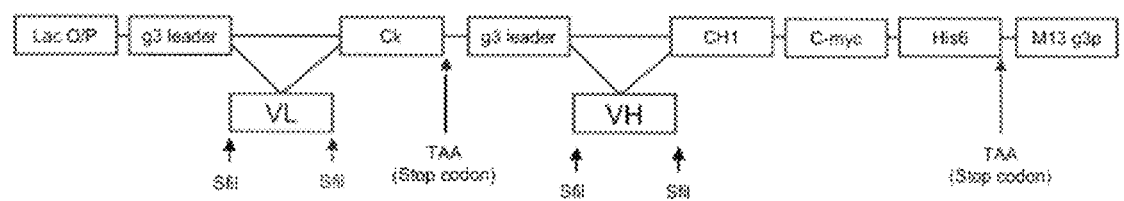
Figure 5:
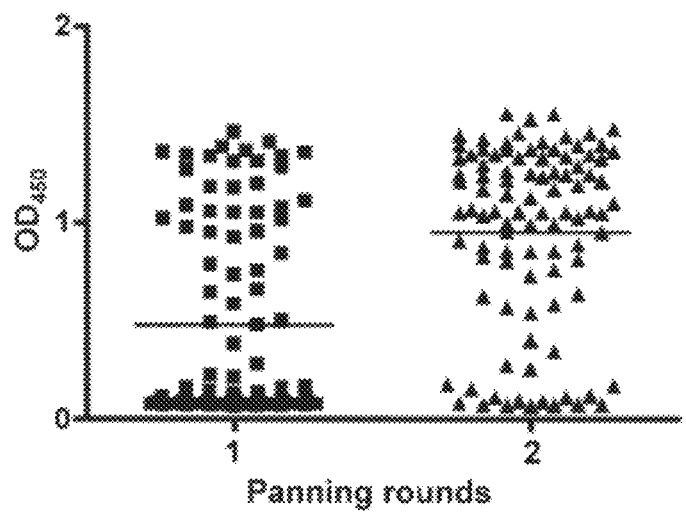
Figure 7:
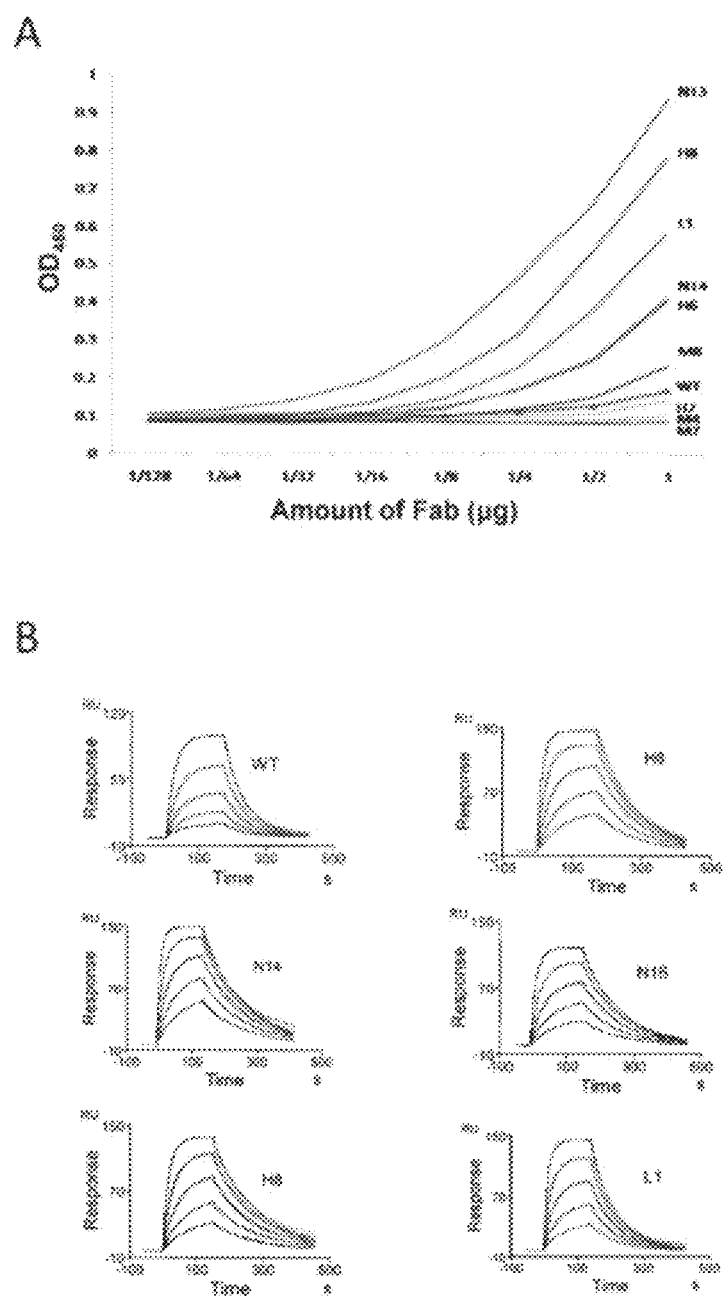

FIG. 1 illustrates nucleic acid (A) and amino acid (B) sequences of aM. CDR1, 2 and 3 as defined by Kabat et al. (15) are underlined: the full amino acid sequences of the variable heavy (VH) and light (VL) chains are given using the standard one-letter code. c, canonical residues; s, somatic mutation; r, rare residue; v, vernier zone residue; Kabat numberings are also included;

Figure 2:
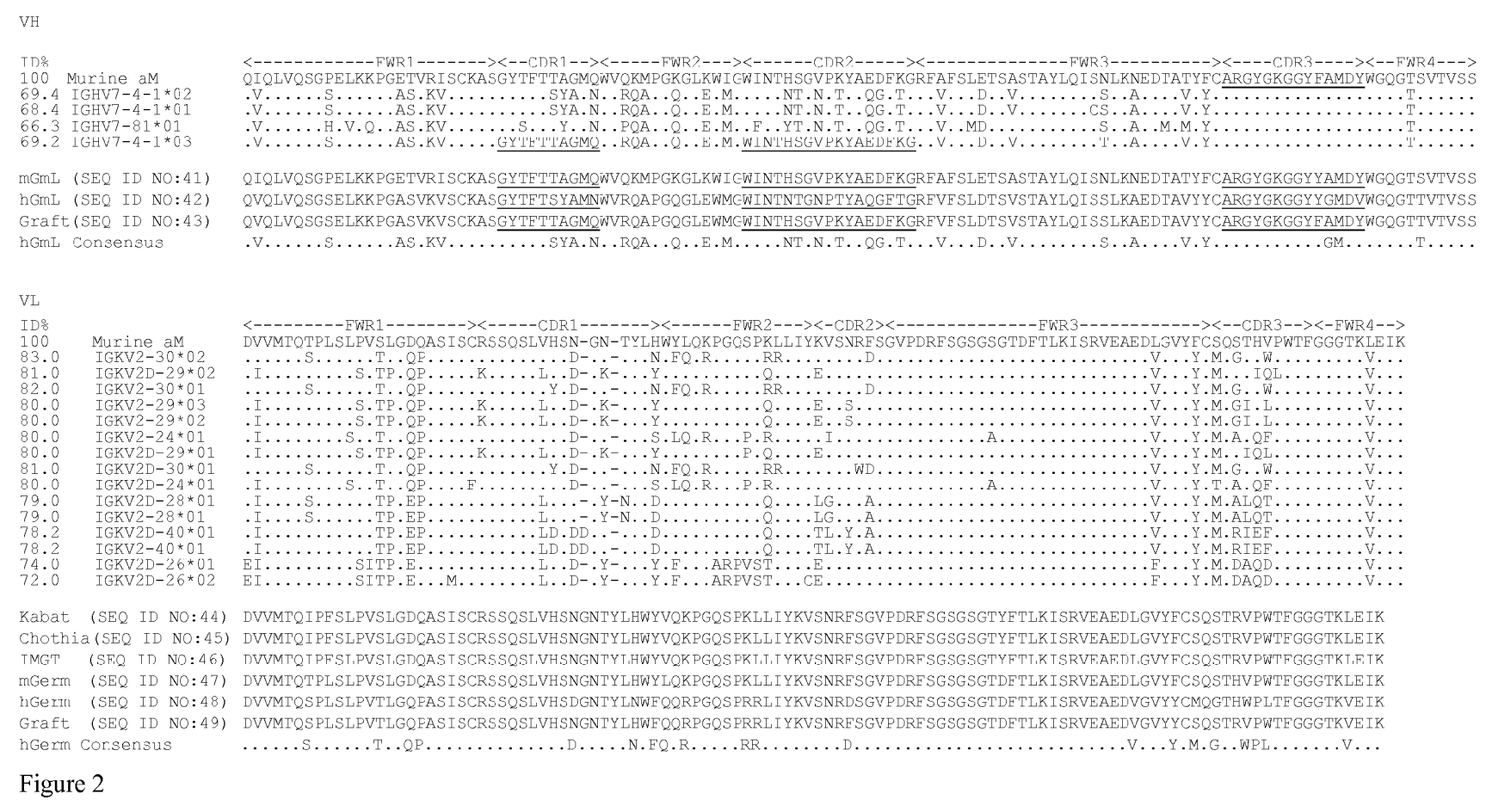

FIG. 2 illustrates the sequence alignment of aM variable regions with the human framework donor antibodies: the amino acid sequences of the murine aM variable regions (murine aM VH, SEQ ID NO: 6; and VL, SEQ ID NO: 8) were used to identify homologous human germline sequences, the numbering of residues and the definition of CDRs were based on Kabat et al. (15); the 4 human germline VH sequences shown are: IGHV7-V-1*02 (SEQ ID NO: 50), IGHV7-4-1*01 (SEQ ID NO: 51), IGHV7-81*01 (SEQ ID NO: 52), IGHV7-4-1*03 (SEQ ID NO: 53), wherein only those positions in which the identity of the amino acid differs from that of murine aM VH are shown in the figure; the 15 human germline VL sequences shown are: IGKV2-30*02 (SEQ ID NO: 54), IGKV2D-29*02 (SEQ ID NO: 55), IGKV2-30*01 (SEQ ID NO: 56), IGKV2-29*03 (SEQ ID NO: 57), IGKV2-29*02 (SEQ ID NO: 58), IGKV2-24*01 (SEQ ID NO: 59), IGKV2D-29*01 (SEQ ID NO: 60), IGKV2D-30*01 (SEQ ID NO: 61), IGKV2D-24*01 (SEQ ID NO: 62), IGKV2D-28*01 (SEQ ID NO: 63), IGKV2-28*01 (SEQ ID NO: 64), IGKV2D-40*01 (SEQ ID NO: 65), IGKV2-40*01 (SEQ ID NO: 66), IGKV2D-26*01 (SEQ ID NO: 67), IGKV2D-26*02 (SEQ ID NO: 68), wherein only those positions in which the identity of the amino acid differs from that of murine aM VL are shown in the figure; the "hGmL Consensus" sequence (SEQ ID NO: 42) is the consensus human germline VH sequence "hGmL" as determined from the alignment of the human germline VH sequences, wherein only those positions in which the identity of the amino acid differs from that of the consensus murine germline VH sequence "mGmL" (SEQ ID NO: 41) are shown in the figure; the "hGerm Consensus" sequence (SEQ ID NO: 48) is the consensus human germline VL sequence "hGerm" as determined from the alignment of the human germline VL sequences, wherein only those positions in which the identity of the amino acid differs from that of the consensus murine germline VL sequence "mGerm" (SEQ ID NO: 47) are shown in the figure;

FIG. 3 illustrates the construction of a framework-assembly library according to an embodiment of the present invention: A. the amino acid sequences of frameworks of the parental murine and selected human germline antibodies; the selected human VH framework (FR) sequences are aligned with the amino acid sequence of murine VH-aM (SEQ ID NO: 6), and the selected human VL FR sequences are aligned with the amino acid sequence of murine VL-aM (SEQ ID NO: SEQ ID NOs: 9-10 correspond to selected human VH FR1 sequences; SEQ ID NOs: 11-12 correspond to selected human VH FR 2 sequences; SEQ ID NOs: 13-16 correspond to selected human VH FR3 sequences; SEQ ID NO: 17 corresponds to the selected human FR4 sequence; SEQ ID NOs: 18-27 correspond to selected human VL FR1 sequences; SEQ ID NOs: 28-34 correspond to selected human VL FR2 sequences; SEQ ID NOs: 35-39 correspond to selected human VL FR3 regions; and SEQ ID NO: 40 corresponds to the selected human VL FR4 sequence; B. PCR strategy for the generation of the framework-assembly library;

FIG. 4 shows phage vector used for the construction of a framework-assembly library according to an embodiment of the present invention: VL and VH genes were inserted into the vector under the control of LacZ promoter, the VH and VL genes were then expressed in-frame with the first constant domain of the human CI heavy chain and the constant domain of the human kappa light chain, respectively;

FIG. 5 illustrates a primary phage display screening according to an embodiment of the present invention: two rounds of phage display panning were performed against c-Myc peptide, after each round of panning, about 100 phage clones were picked randomly from the eluted phage pools, each phage clone was amplified and subjected to ELISA assay for their binding to c-Myc;

FIG. 6 illustrates affinity ranking according to an embodiment of the present invention: A. primary structure of the FASEBA vector, which contains a capture tag (BSA12) and a detection tag (His tag); B. Affinity ranking of the Fab clones from the FASEBA library: BSA was immobilized on the surface of CM-5 sensor chips, to be captured Fab-BSA12 fusions were then injected over the surface of the chips; c-Myc-containing recombinant protein was injected and the surface plasmon resonance (SPR) profiles were recorded, the SPR data of different Fab-BSA12 proteins were analyzed using BIAevaluation 3.0 software, WT1 indicates the parental murine mAb;

FIG. 7 illustrates the characterization of soluble humanized Fabs according to an embodiment of the present invention: A. ELISA analysis of the binding capacity of solube Fabs with the antigen; B. determination of the SRP profiles of the Fabs; non-red lines represent the real SPR profiles, whereas red lines represent their 1:1 fitting curves; and FIG. 8 shows humaness evaluation by ELISA according to an embodiment of the present invention: purified murine and humanized Fabs were coated on ELISA plates, after washing and blocking, Fabs bound on the plates were detected by goat anti-human IgG/HRP, OD value was measured at 450 nm.

DETAILED DESCRIPTION OF THE INVENTION

Unless defined otherwise, all technical and scientific terms used herein have the same meaning as commonly understood to one of ordinary skill in the art to which this invention pertains. Otherwise, certain terms used herein have the meanings as set in the specification. All patents, published patent applications and publications cited herein are incorporated by reference as if set forth fully herein. It must be noted that as used herein and in the appended claims, the singular forms "a," "an," and "the" include plural reference unless the context clearly dictates otherwise.

As mentioned previously, there are two main genres of humanization methods, namely, rational and empirical methods (16). Rational methods usually involve designing of a humanized antibody variant to be tested for binding or any other property of interest. If the designed variants prove to be unsatisfactory, a new design cycle and binding assessment is initiated. The key factor to succeed in the design cycle is the structural and physicochemical compatibility between residues targeted for transferring the specificity from a given nonhuman antibody to the human one. The other humanization method is empirical method. The success of this method depends on the generation of a large antibody library.

Another major issue during antibody humanization is the complete or partial loss of binding affinity of parental antibody to the antigen. In many cases, antibody humanization changes antibody conformation and hence results in structural instability and low expression level of humanized antibody. Expression level is another important property for a humanized antibody. High expression level of antibody will reduce the downstream cost of antibody production greatly.

To overcome the problems of the conventional rational and empirical methods, a new strategy to generate humanized antibodies is developed in the present invention. This method, designated framework-assembly, does not require knowledge of antibody structure and hence bypasses the uncertainty of rational methods. At the same time, this method does not require a big antibody library. For example, desirable humanized antibodies were obtained from a framework library containing a reasonable number of clones, e.g., only 5,600 clones, that can be easily covered by a single transformation. The humanized antibodies displaying higher antigen binding affinity and higher expression level than the parental non-human antibody are easily screened by combining phage display selection, Fast Screen for Expression, Biophysical-properties and Affinity (FASEBA) and affinity ranking technologies. The framework-assembly method according to embodiments of the present invention is easier to implement and more efficient than the conventional rational and empirical methods.

As used herein, a "homologous human germline VH" refers to the heavy chain variable domain (VH) of a human germline antibody that has at least 60% sequence identity to the amino acid sequence of the VH of the non-human antibody of interest, or the "parental antibody."

As used herein, a "homologous human germline VL" refers to the light chain variable domain (VL) of a human germline antibody that has at least 60% sequence identity to the amino acid sequence of the VL of the non-human antibody of interest.

As used herein, a "corresponding framework (FR)" refers to a framework generally corresponding to the same structural location in another antibody. For example, an FR1, FR2, FR3 or FR4 in one or more homologous human germline VHs is a "corresponding FR" of an FR1, FR2, FR3 or FR4 in a humanized VH, respectively; and an FR1, FR2, FR3 or FR4 in one or more homologous human germline VLs is a "corresponding FR" of an FR1, FR2, FR3 or FR4 in a humanized VL, respectively.

As used herein, a "corresponding complementarity determining region (CDR)" refers to a complementarity determining region generally corresponding to the same structural location in another antibody. For example, a CDR1, CDR2 or CDR3 in the VH of a non-human antibody is a "corresponding CDR" of a CDR1, CDR2 or CDR3 in a humanized VH, respectively; and a CDR1, CDR2 or CDR3 in the VL of a non-human antibody is a "corresponding CDR" of a CDR1, CDR2 or CDR3 in a humanized VL, respectively.

As used herein, "Fast Screen for Expression, Biophysical-properties and Affinity system" or "FASEBA system" refers to a technology or system that can be used to isolate humanized antibody clones having high expression level in an expression cell. As illustrated in FIG. 6A, the FASEBA system utilizes a vector encoding two components: a capture tag, such as a bovine serum albumin single domain antibody (BSA12), and a detection tag, such as a His tag. BSA12 can bind bovine serum albumin (BSA) with a very high affinity, thus immobilizing BSA12-fused proteins on BSA-coated solid surface, such as an ELISA plate, through the interaction between BSA12 and BAS. The detection tag, such as the His tag, is used to facilitate the evaluation of the amount of captured BSA12-fused proteins, for example, by using an anti-His tag antibody B. FASEBA can be performed on any solid surfaces, such as microtiter plates, making high throughput screening of expression level feasible.

It is readily appreciated by those of ordinary skill in the art that other capture tags and detection tags can also be used in the FASEBA system.

Embodiments of the present invention relate to an improved method for producing humanized antibody or an antigen binding fragment thereof for a non-human antibody to an antigen. The method comprises: (1) constructing a heavy chain variable domain (VH) framework (FR) library comprising nucleic acids encoding a diversity of VHs, each of the VHs comprising FR1, FR2, FR3 and FR4 independently selected from corresponding FRs of a first number of homologous human germline VHs, and corresponding complementarity determining regions (CDRs) of the VH of the non-human antibody; (2) constructing a light chain variable domain (VL) FR library comprising nucleic acids encoding a diversity of VLs, each of the VLs comprising FR1, FR2, FR3 and FR4 independently selected from corresponding FRs of a second number of homologous human germline VLs, and corresponding CDRs of the VL of the non-human antibody; (3) constructing a framework-assembly library comprising nucleic acids encoding a diversity of Fabs or fragments thereof, each of the Fabs or the fragments thereof comprising a VH encoded by a nucleic acid in the VH FR library and a VL encoded by a nucleic acid in the VL FR library; (4) expressing the framework-assembly library in host cells; (5) identifying from the expressed framework-assembly library an Fab or a fragment thereof that binds to the antigen; (6) identifying the VH and VL in the identified Fab or the fragment thereof as a humanized VH and a humanized VL, respectively, for the humanized antibody or the antigen binding fragment thereof; and (7) producing the humanized antibody or the antigen binding fragment thereof comprising the identified humanized VH and the humanized VL.

The sequence information of any given non-human antibody can be obtained by various means known to those skilled in the art, such as by direct cloning and sequencing, or by searching a sequence database. The amino acid sequence of the heavy chain variable domain (VH) or light chain variable domain (VL) of the non-human antibody can be used to obtain sequence information about the homologous human germline VHs or homologous human germline VLs, respectively.

For example, the amino acid sequence of the VH of the non-human antibody is aligned with a plurality of amino acid sequences of VHs of human germline antibodies. The human germline VHs having at least about 60% sequence identity to the VH of the non-human antibody are selected as homologous human germline VHs for the present invention. Homologous human germline VLs can be selected using a similar method.

The threshold sequence identity used to select homologous human germline VHs and VLs can be the same or different. It can be adjusted depending on factors such as the sequences of the VH and VL of the non-human antibody of interest, the sequences of available VHs and VLs of human germline antibodies, the desirable size of the library, etc. The selected homologous human germline VH and VL can be from the same human germline antibody or different human germline antibodies. Preferably, at least two homologous human germline VHs having the most sequence identity to the non-human VH and at least two homologous human germline VLs having the most sequence identity to the non-human VL are selected.

Examples of homologous human germline VHs that can be used in the present invention include, but are not limited to, VHs of human germline antibodies having at least about 60%, 65%, 70%, 75%, 80%, 85%, 90%, 95% or 100% sequence identity to the amino acid sequence of the VH of the parental non-human antibody. Preferably, each of the complementarity determining regions (CDRs) in the homologous human germline VH has the same length as that in each of the corresponding CDRs in the VH of the parental antibody. Also preferably, the homologous human germline VH does not contain any of proline, which introduces rigidity into the polypeptide chain; cysteine, which introduces potential for oxidative damage; and potential N-glycosylation site.

Examples of homologous human germline VLs that can be used in the present invention include, but are not limited to, VLs of human germline antibodies having at least about 60%, 65%, 70%, 75%, 80%, 85%, 90%, 95% or 100% sequence identity to the amino acid sequence of the VL of the parental antibody. Preferably, each of the complementarity determining regions (CDRs) in the homologous human germline VL has the same length as that in each of the corresponding CDRs in the VL of the parental antibody. Also preferably, the homologous human germline VL does not contain any of proline, which introduces rigidity into the polypeptide chain; cysteine, which introduces potential for oxidative damage; and potential N-glycosylation site.

According to an embodiment of the present invention, the homologous human germline VHs have at least about 60% sequence identity to the VH of the non-human antibody, and the homologous human germline VLs have at least about 70% sequence identity to the VL of the non-human antibody.

The VH or VL framework (FR) library can be constructed using any method known in the art in view of the present disclosure. In an embodiment of the present invention, a VH framework library is constructed by overlapping polymerase chain reaction (PCR) using a mixture of templates comprising nucleotide sequences encoding each and all corresponding frameworks (FRs) of the homologous human germline VHs, and each and all corresponding complementarity determining regions (CDRs) of the non-human VH to generate nucleic acids encoding VHs. Each of the VHs contains FR1 CDR1 FR2 CDR2 FR3 CDR3 FR4, with FR1, FR2, FR3 and FR4 from one or more homologous human germline VHs, and CDR1, CDR2 and CDR3 from the non-human VH.

In another embodiment of the present invention, a VL framework library is constructed by overlapping PCR using a mixture of templates comprising nucleotide sequences encoding each and all corresponding FRs of the homologous human germline VLs and each and all corresponding CDRs of the non-human VL to generate nucleic acids encoding VLs. Each of the VLs contains FR1 CDR1 FR2 CDR2 FR3 CDR3 FR4, with FR1, FR2, FR3 and FR4 from one or more homologous human germline VLs, and CDR1, CDR2 and CDR3 from the non-human VL.

The diversity of the VH FR library and the diversity of the VL FR library can be same or different.

The framework-assembly library can be constructed using any method known in the art in view of the present disclosure. In one embodiment of the present invention, nucleotide sequences in the VH FR library and VL FR library are cloned into an expression vector, such as a phagemid vector, during the construction of the framework-assembly library. Preferably, the expression vector allows for expression of an Fab or an Fab fragment that contains a VH and VL from the VH FR library and VL FR library, respectively. The Fab or Fab fragment contains one or more constant domains of a heavy chain and one or more constant domains of a light chain of one or more antibodies, preferably, human antibodies. In a preferred embodiment, the Fab or Fab fragment comprises the first constant domain of a human IgG1 heavy chain (hIgG1CH1) fused in frame with the humanized VH, and the constant domain of human IgK light chain (hIgKCL) fused in frame with the humanized VL.

The framework-assembly library can be expressed by any expression method known in the art in view of the present disclosure. Preferably, the expression is under the control of one or more regulatable promoters. The host cell for the expression can be any suitable cells, such as a bacterial cell, a yeast cell or a mammalian cell. Preferably, the host cell is *Escherichia coli*. In view of the present disclosure, any method known in the art can be used to introduce nucleic acids in the framework-assembly library into a host cell, such as transformation, transduction, electroporation, etc.

The expressed framework-assembly library can be screened for an Fab or a fragment thereof that binds to the antigen of interest. The humanized VH and the humanized VL that bind to the antigen can be further identified from the Fab or fragment thereof. In an embodiment of the present invention, the framework-assembly library is expressed and the humanized VH and VL that bind to the antigen are selected by phage-display, preferably with two or more rounds of selection.

In an embodiment of the present invention, more than one Fabs or fragments thereof that bind to the antigen of interest are identified. Additional assays or measurements are conducted to further identify the Fab or fragment thereof for subsequent production of the humanized antibody.

In one embodiment of the present invention, the method further comprises measuring expression level of each of the more than one Fabs or fragments thereof in an expression cell, and identifying the VH and VL within the Fab or fragment thereof that has the highest expression level as the humanized VH and the humanized VL, respectively.

In a preferred embodiment, each of the more than one Fabs or fragments thereof are subjected to expression screening by using an FASEBA system. FASEBA is a patented technology platform which is capable of screening expression level and other biophysical properties in a high throughput fashion.

In another embodiment of the present invention, the method further comprises selecting a Fab or fragment thereof having a high binding affinity to the antigen of interest. For example, after an FASEBA screening, affinity ranking is conducted to further identify humanized VH and VL having high binding affinity to the antigen.

Another general aspect of the invention relate to a humanized antibody or an antigen binding fragment thereof produced by a method according to an embodiment of the present invention. The humanized antibody or the antigen binding fragment thereof can be a humanized monoclonal or polyclonal antibody or antigen binding fragment thereof.

In an embodiment of the present invention, the humanized antibody is a humanized rodent antibody, such as a murine mAb that binds specifically to huamn c-Myc, preferably selected from the group consisting of clones H6, H8, L1, N13, and N14 described herein.

In an embodiment of the present invention, the humanized antibody or antigen binding fragment thereof has a higher binding affinity to the antigen than the non-human antibody, or the parental antibody.

Another general aspect of the invention relates to a composition comprising a humanized antibody or an antigen binding fragment thereof according to an embodiment of the present invention. The composition can be used for any purposes, such as for diagnostic, treatment or basic research.

Another general aspect of the invention relates to a method of using a humanized antibody or an antigen binding fragment thereof according to an embodiment of the present invention. The method comprises contacting the humanized antibody or the antigen binding fragment thereof with the antigen.

The method can be a diagnostic method. For example, the antigen is present in a biological sample, in vivo or in vitro, and the method further comprises detecting the binding between the antibody or the antigen binding fragment thereof with the antigen.

The method can also be a therapeutic method. For example, the antigen is present in the subject, such as a target for treatment of a disease, the humanized antibody or an antigen binding fragment thereof is administered to a subject in need of the treatment. The binding between the humanized antibody or an antigen binding fragment thereof with the antigen results in the treatment of the disease.

Another general aspect of the invention relates to a framework-assembly library for a non-human antibody to an antigen. The library comprises nucleic acids encoding a diversity of Fabs or fragments thereof, each of the Fabs or the fragments thereof comprising a VH and a VL, wherein the VH comprises framework 1 (FR1), FR2, FR3 and FR4 independently selected from corresponding FRs of a first number of homologous human germline VHs and corresponding complementarity determining regions (CDRs) of the VH of the non-human antibody, and the VL comprises FR1, FR2, FR3 and FR4 independently selected from the corresponding FRs of a second number of homologous human germline VLs and corresponding CDRs of the VL of the non-human antibody.

According to an embodiment of the present invention, the number of homologous human germline VHs and the number of homologous human germline VLs used in the library can be same or different.

In a preferred embodiment of the present invention, the diversity of the library is reasonably small. For example, the diversity of the library can be less than 10,000. Embodiments of the invention also include diversity of the library less than 9,000, 8,000, 7,000, 6,000, 5,000, etc.

The following examples illustrate the invention but are in no way intended to limit the scope of the present invention.

EXAMPLES

Methods

Cloning and Sequencing of the Parental Monoclonal Antibody

A murine hybridoma cell line secreting a monoclonal antibody raised against c-Myc peptide was generated in GenScript Inc (Cat. No. RP11731). This mouse mAb is referred to herein as aM.

Total RNA was extracted from aM hybridoma cells using TRIzol (Invitrogen, Carlsbad, Calif.). cDNA was generated by reverse transcription using Omniscript RT Kit (QIAGEN, Shanghai, China). The VH and VL genes of aM were amplified by PCR using the following primer sets: for amplification of VL gene, the forward primer is 5'-TTATTACTCGCGGC-CCAGCCGGCC-3' (SEQ ID NO:1) and the reverse primer is 5'-GGTGCAGCCA CCGTACGTTTGATTTC-3' (SEQ ID NO:2); for amplification of VH gene, the forward primer is 5'-CATGGCCGAGGTGCAGCTGGCTAGC-3' (SEQ ID NO:3) and the reverse primer is 5'-TGCGGCCCCA TTTGCGGCCGCAGAG-3 (SEQ ID NO:4). The PCR products of VH and VL genes were then cloned into pUC57-T vector and sequenced. The sequence results are shown in FIG. 1.

Selection of the Human Frameworks

In order to select human heavy chain variable (VH) and light chain variable (VL) frameworks for aM humanization, the VH and VL amino acid sequences of aM, SEQ ID NO: 6 and SEQ ID NO:8, respectively, were separately subjected to IgBlast (world wide web: IMGT.org) analysis. Homologous human germline antibody heavy and light chain framework segments having a threshold or higher than the threshold sequence identity to those of murine aM frameworks were selected (FIG. 2).

Construction of the Framework-Assembly Libraries

A VH framework (FR) library and a VL framework (FR) library were constructed separately and then assembled into phagemid to make a Fab framework-assembly library.

The VH FR library contained nucleotide sequences encoding a plurality of VHs. Each VH had FR1, FR2, FR3 and FR4 each independently selected from the corresponding FRs of the selected homologous human germline VHs and complementarity determining regions (CDRs) of aM VH. For the construction of the VH FR library, the coding sequences for the 4 frameworks, FR1, FR2, FR3 and FR4, of each of the selected homologous human germline antibody heavy chain framework segments were separately PCR amplified. The amplified FR1, FR2, FR3 and FR4 coding sequences of all selected human germline antibody heavy chain framework segments were mixed with the coding sequences for the CDRs of aM VH. DNAs in the mixture were used as templates for overlapping PCR for the production of nucleotide sequences encoding VHs having FRs of one or more human germline VHs and CDRs of aM VH. The strategy of overlapping PCR of VH genes was shown in FIG. 3.

The VL FR library contained nucleotide sequences encoding a plurality of VLs. Each VL had FR1, FR2, FR3 and FR4 each independently selected from the corresponding FRs of the selected homologous human germline VLs and CDRs of aM VL. The procedure of constructing VL FR library was similar to that of constructing VH FR library. The coding sequences for the 4 frameworks, FR1, FR2, FR3 and FR4, of each of the selected homologous human germline antibody light chain framework segments were separately PCR amplified. The amplified FR1, FR2, FR3 and FR4 coding sequences of all selected human germline antibody light chain framework segments were mixed with the coding sequences for the CDRs of aM VL. DNAs in the mixture were used as templates for overlapping PCR for the production of nucleotide sequences encoding VLs having FRs of one or more human germline VLs and CDRs of aM VL.

The primers used for the construction of VH and VL framework library are listed in Table 1.

TABLE 1

Binding kinetics of aM and its humanized Fabs

| Antibody | ka (1/Ms) | kd (1/s) | $K_D$ (M) | Fold change |
|---|---|---|---|---|
| WT | $1.6 \times 10^5$ | $1.8 \times 10^{-2}$ | $1.1 \times 10^{-7}$ | 1 |
| N14 | $4.8 \times 10^5$ | $7.2 \times 10^{-3}$ | $1.5 \times 10^{-8}$ | 7.3 |
| N13 | $3.3 \times 10^5$ | $7.0 \times 10^{-3}$ | $2.1 \times 10^{-8}$ | 5.2 |
| H6 | $3.8 \times 10^5$ | $8.9 \times 10^{-3}$ | $2.3 \times 10^{-8}$ | 4.8 |
| H8 | $2.9 \times 10^5$ | $7.8 \times 10^{-3}$ | $2.7 \times 10^{-8}$ | 4.1 |
| L1 | $3.4 \times 10^5$ | $9.7 \times 10^{-3}$ | $2.9 \times 10^{-8}$ | 3.8 |

Cloning of the V Regions into Phage Vectors

The PCR amplified nucleotide sequences encoding full length VHs and VLs were digested with SfiI and ligated into a conventional phagemid vector constructed at GenScript Inc. to generate phage-displayed Fab library. This vector allowed for the expression of Fab fragments that contain the first constant domain of a human heavy chain (hIgG1CH1) and the constant domain of human light chain (hIgKCL) under the control of the LacZ promoter (FIG. 4).

After transformation, bacteria harboring the phage library were grown in liquid media containing 100 µg/ml ampicillin and 25 µg/ml kanamycin at 37° C. and rescued by infection with helper phage (M13KO7). Phage particles were precipitated from the supernatant by adding 0.2 volume of polyethyleneglycol (PEG) 8000 and 2.5 M NaCl, and were resuspended in PBS.

Phage-Displayed Library Panning

Antigen (c-Myc peptide, generated at GenScript Inc.) was biotinylated and then immobilized on the microtiter plates pre-coated with streptavidin. Antigen coated plates were then blocked with 2% (w/v) skimmed milk powder in PBS (2% MPBS). Phage library containing $10^{11}$ phage particles was added to the plates and were incubated for 2 hours at room temperature. Non-bound phage were removed by washing 10-20 times with PBS containing 0.1% Tween 20 (PBS-T), followed by 10~20 times washing with PBS. Bound phage were eluted by incubation with 100 µl of 100 mM triethylamine (TEA) for 10 min, followed by neutralization immediately with 50 µl of 1 M Tris-HCl, pH 7.5. Eluted phages were used to infect exponentially growing E. coli TG1 cells by incubating for 30 min at 37° C. without shaking. Infected cells were spread on TYE plates containing ampicillin (100 µg/ml) and glucose (1% w/v), then the plates were incubated overnight at 37° C. Individual phage-infected clones were picked and grown for production of phage particles in 96-well microtiter plates. The culture was rescued using M13K07 helper phage. Rescued phage particles were used to test their antigen recognition properties by ELISA or to initiate subsequent rounds of selection under similar conditions. Two rounds of selection were typically performed.

ELISA Screening of Selected Clones

In order to detect antigen recognition, microtiter plates were coated with 10 µg/ml of antigen. After overnight incubation at 4° C., the plates were blocked with 2% MPBS for 1 hour at RT followed by three washes with PBS. The selected phage preparation was diluted 1:2 in 4% MPBS before adding into each well, and incubated for 1 hour at RT. The plates were washed three times with PBS-T, followed by three times with PBS, and incubated with a 1:5,000 dilution of a mouse anti-M13 phage-horseradish peroxidase (HRP) conjugate (GE Healthcare, Uppsala, Sweden) in 2% MPBS. The plates were washed 3 times with PBS, followed by adding 100 µl of tetramethylbenzidine (TMB) solution to each well and incubate for 15 min. Reaction was stopped by adding 100 µl of 1 M sulphuric acid. ELISA reading was recorded by measuring absorption at 450 nm with an ELISA reader.

Expression Screening

Phages obtained from the pannings were amplified in TG1 E. coli cells. Phagemids were prepared subsequently. The Fab fragments in phagemid were subcloned into FASEBA vector for expression screening. This vector allows for expression of an antibody fused to BSA12, a single domain camelid antibody, which binds BSA with an affinity of 4 pM (FIG. 6A).

The FASEBA vectors containing Fab-BSA12-His fusions were subsequently transformed for soluble expression in E. coli TG1. Overnight grown E. coli culture were diluted 10 times in 2x YT medium containing 2% glucose and cultured for 1 h at 30° C. The harvested bacterial pellets were then resuspended in equal volume of fresh 2× YT medium (without glucose) containing 1 mM IPTG, and induced overnight. The cell culture supernatants containing Fab were collected.

100 µl supernatant of each well was transferred to an ELISA plate coated with 3% BSA. Fab was captured on ELISA plate attributed to the interaction between BSA12 and BSA. The amount of Fab captured was then determined by ELISA using goat anti-His tag antibody.

Affinity Ranking and Kinetics Analysis

The antigen-binding affinity of humanized Fab variants and parental antibody was measured by surface plasmon resonance on a Biacore T200 (GE Healthcare, Uppsala, Sweden). For affinity ranking, research-grade CM5 sensor chips and Amine Coupling Kits were obtained from GE Healthcare. For affinity ranking analysis, BSA was immobilized on CM5 chip. A recombinant protein containing c-Myc tag was used as antigen for affinity screening and measurement. The Fab-BSA12 fusions were captured on the chip surface by interacting with BSA. c-Myc antigen was then injected (1 min association, 5 min dissociation) over the Fab surfaces at a flow rate of 30 µl/min.

For precise analysis of purified Fabs, the c-Myc-containing recombinant protein was immobilized on the sensor chip. Binding assays were performed by injection of soluble Fab candidates at various concentrations. After each binding measurement, residual Fab was removed by washing with 20 µl of 10mM glycine-HCl (pH 1.5) at a flow rate of 20 µl/min. Each data set was fitted globally to a simple 1:1 Langmuir binding model using BIAevaluation software 3.0 (GE HealthCare, Uppsala Sweden).

Assessment of "Humanness" by Z-Score Analysis and ELISA

Abhinandan and Martin (10), proposed a method to assess the "degree of humanness" of antibody sequences providing a tool that may assist predictions of immunogenicity. The Z-score defines the final measure of how typical a sequence is to the human repertoire. We compared the Z-scores of our humanized Fab sequence (VH and VL) with Z-scores of the original murine aM-VH and VL sequence by bioinf.org.uk world web based server (bioinf.org.uk/abs/shab/).

For ELISA assay, the parental murine or humanized Fabs were coated directly on the ELISA plates. After washing thoroughly with PBS, the amount of Fabs absorbed on ELISA plates was determined by using goat anti-human IgG/HRP. ELISA reading was recorded by measuring absorption at 450 nm with an ELISA reader.

Results

Sequence of aM VH and VL

The VH and VL genes of aM were sequenced (FIG. 1A). The key amino acid residues, including canonical residues, somatic mutation, rare residue and vernier zone residues of aM were determined according to previous reports (11-14) and were marked in FIG. 1B. The numbering of residues and CDR determination of the antibody is based on Kabat et al. (15).

Selection of Frameworks

To select suitable human variable domains that should serve as framework donors, the amino acid sequences of aM VH and VL were independently aligned against the entire repertoire of human antibody sequences contained in the IMGT database using IgBlast search. We used germline sequences for templates rather than non-germline sequences in order to eliminate potential immunogenicity of somatic mutations. The human antibody sequences were arranged in order of sequence identity to the parental murine antibody. We independently selected multiple germline templates which show the highest sequence identity to the parental murine antibody. From this list, human sequences with different CDR lengths with parental murine antibody are discarded. Sequences containing: (a) unusual proline (introduces rigidity into the polypeptide chain); (b) cysteine (introduces potential for oxidative damage) residues; and (c) potential N-glycosylation sites are further excluded. By collating all of the above data and comparing the best candidates for conservative change at each mismatched residue, 4 human VH germline and 15 human VL germline sequences were selected, respectively. More precisely, these included: heavy chain: IGVH7-4-101, IGVH7-4-102, IGVH7-4-103 and IGVH7-81-01; light chain: IGKV2-3002, IGKV2D-2902, IGKV2-3001, IGKV2-2903, IGKV2-2902, IGKV2-2401, IGKV2D-2901, IGKV2D-3001, IGKV2D-2401, IGKV2D-2801, IGKV2-2801, IGKV2D-4001, IGKV2-4001, IGKV2D-2601 and IGKV2D-2602.

Construction of Framework-Assembly Libraries

Among the fifteen selected VL germlines, there are ten different FR1, seven different FR2 and five different FR3. The FR4s in all VL germlines are the same. Among the four selected VH germlines, there are two different FR1, two different FR2 and four different FR3. All VH germlines have the same FR4.

All the FRs of VH and VL genes were PCR amplified by using the primers listed in Table 1. Each FR of VL or VH was randomly assembled with the aM VL or VH CDRs, as well as other FRs and CDRs to generate VL/VH framework-assembled libraries, respectively. The diversity of VL framework library is 350 (10×7×5) while the diversity of VH library is 16 (2×2×4). VH and VL libraries were assembled sequentially into a phagemid vector, resulting in a phage-displayed Fab library with a diversity of 5,600 different clones (FIGS. 3 and 4). In a single transformation, we obtained $5 \times 10^6$ clones which is about 1000 times higher than the theoretical library size and is sufficient to cover the whole library.

Primary Phage Display Screening

The constructed aM framework assembly phage library was screened on c-Myc peptides coated on microtiter plates. Two rounds of selection were performed. After each round of selection, about 100 phage clones were picked and subjected to ELISA assay to evaluate their binding capacity to the c-Myc peptide. The average OD value of the phages from the $1^{st}$ round is about 0.45 while that from the $2^{nd}$ round is 0.95 (FIG. 5), indicating the enrichment of c-Myc specific phages through the panning process.

Secondary Expression Screening

To further isolate Fab clones with high expression level in E. coli, the Fabs from the pool of the $2^{nd}$ round of phage display panning was recloned into FASEBA vector for expression screening (FIG. 6A).

To perform FASEBA screening, microtiter plates were coated with BSA. The cell culture supernatant containing Fab-BSA12 fusions were then added into each well and incubation was allowed at RT for one hour. After wash, Fabs captured on microtiter plates were determined by incubation with anti-His IgG/HRP and TMB. OD450 was measured.

Among the approximately 1,000 clones tested, 720 clones displayed a higher expression level than that of the wild type Fab clone (data not shown). Out of the 720 clones, the top 40 were selected for affinity ranking.

Affinity Ranking

To perform affinity ranking, Fabs from FASEBA screening were injected over the surface of CM5 sensor chip pre-coated with BSA. Fabs, which were fused to BSA12, were then captured on CM5 chip due to the binding between BSA and BSA12. Antigen at different concentrations was injected and the interaction profiles between the Fabs and the antigen were recorded and analyzed (FIG. 6B). 40 Fab-BSA12 clones were tested and most humanized Fabs displayed higher affinity than parental murine Fab. The top 10 Fab clones with the highest affinity were listed in FIG. 6B.

To measure the accurate affinities of the top 10 Fab clones, the BSA12 protein tag attached to them were removed by standard subcloning. The soluble Fabs were expressed in *E. coli* and purified, followed by ELISA determination for their binging to the antigen. Out of 10 Fab clones investigated, 5 clones showed higher ELISA reading than the parental murine Fab (FIG. 7A) at the same protein concentration.

Kinetic Analysis

The 10 Fabs with the strongest binding to the antigen as identified by ELISA were further characterized by SPR. Five different concentrations of Fabs (80, 40, 20, 10, 5 nM in 1×HBS-EP) were tested. The Fabs were injected over the surfaces with pre-immobilized antigen. The dissociation phase was monitored for 6 min (FIG. 7B). All the tested Fabs demonstrate good 1:1 Langmuir fitting. The kinetics data of humanized Fabs and the parental murine Fab were listed in Table 2.

TABLE 2

Sequence comparison of humanized Fabs with the parental murine antibody.

| Clone | | Closest human germline | Identity % (a) | Identity % (b) | Improvement % |
|---|---|---|---|---|---|
| N13 | VH | IGHV7-4-1*02 | 84.7 | 69.4 | 15.3 |
| | VL | IGKV2D-29*02 | 85 | 81 | 4 |
| N14 | VH | IGHV7-4-1*02 | 84.7 | 69.4 | 15.3 |
| | VL | IGKV2D-29*01 | 87 | 80 | 7 |
| H8 | VH | IGHV7-4-1*02 | 87.8 | 69.4 | 18.4 |
| | VL | IGKV2-18*01 | 88 | 80 | 8 |
| H6 | VH | IGHV7-81*01 | 84.7 | 66.3 | 18.4 |
| | VL | IGKV2D-29*02 | 86 | 80 | 6 |
| L1 | VH | IGHV7-4-1*02 | 86.7 | 69.4 | 17.3 |
| | VL | IGKV2-24-*01 | 85 | 80 | 5 |

(a) amino acid sequence identity of humanized clones with closest human germline;
(b) amino acid sequence identify of original murine antibody with human germlines.

The calculated $K_D$ for the humanized variants ranged from 3 to 7 folds lower than that of parental Fab. These results demonstrate that humanized Fab variants have higher binding affinities than the parental antibody.

Humaness Evaluation

To evaluate the humanness of the humanized Fabs, we compared the amino acids sequence of humanized Fabs with human germline sequences (Table 3).

TABLE 3

Evaluation of humaness by Z-score

| Antibody | ID | Z-Score VL | Z-Score VH |
|---|---|---|---|
| Murine Fab | WT | −1.863 | −1.669 |
| Humanized Fab | N16 | −1.244 | −0.515 |
| | L1 | −1.536 | −0.289 |
| | N14 | −1.37 | −0.367 |
| | H8 | −1.487 | −0.367 |
| | H6 | −1.482 | −0.367 |

The data in Table 3 showed clearly that all the 5 humanized Fab clones displayed higher sequence identity with human germline antibody sequence than the parental murine antibody. The sequence identity of the VH sequences to its closest human germline sequence increased by 15.3~18.4% while the similarity of VL sequence increased by 4.0~8.0%.

Recently, Z-score was proposed by Abhinandan and Martint as a tool to evaluate antibody humanness (10). The Z-score was defined as the measure of how typical a sequence is of the human repertoire. A Z-score of zero represents a sequence which shows average similarity to the repertoire of human sequences. Positive Z-scores represent sequences that, on average, show higher sequence identity with other human sequences, and negative Z-scores represent sequences with less typically human character.

The Z-score of the parental murine (WT) and humanized Fabs was listed in Table 3. VHs and VLs of humanized Fabs are lower than that of the parental murine antibody, suggesting the increase of humaness of humanized Fabs. It is noteworthy that the Z-score of VH of humanized Fab is lower than that of VL.

We further developed an ELISA assay to evaluate the humaness of the antibodies. Our hypothesis is that if an antibody contains more humanized amino acid residues, it should be easier to be recognized by anti-human antibodies. Therefore, purified murine and humanized Fabs were directly coated on ELISA plates. The Fabs on plates were then detected by rabbit anti-human IgG/HRP. The ELISA readings correlate to the extent of humanness of the engineered antibodies (FIG. 8). Among the tested clones, H6, H8, L1, N13, and N14 had higher OD value than the parental murine (WT), suggesting these Fabs contain more humanized amino acids. These data are consistent with the results obtained in the Z-score analysis.

The method described here serves as a universal approach for humanization of other antibodies more efficiently.

REFERENCES

1. Kohler, G., and Milstein, C. (1975) Continuous cultures of fused cells secreting antibody of predefined specificity, *Nature* 256, 495-497.
2. Pimm, M. V., Leong, K. S., and Markham, A. J. (1990) A passive haemagglutination test for human anti-mouse antibody (HAMA) responses in patients undergoing immunoscintigraphy, *Nucl Med Commun* 11, 121-126.
3. Khazaeli, M. B., Conry, R. M., and LoBuglio, A. F. (1994) Human immune response to monoclonal antibodies, *J Immunother Emphasis Tumor Immunol* 15, 42-52.
4. Carroll, W. L., Thielemans, K., Dilley, J., and Levy, R. (1986) Mouse×human heterohybridomas as fusion partners with human B cell tumors, *J Immunol Methods* 89, 61-72.
5. Rader, C., Cheresh, D. A., and Barbas, C. F., 3rd. (1998) A phage display approach for rapid antibody humanization: designed combinatorial V gene libraries, *Proc Natl Acad Sci USA* 95, 8910-8915.
6. Niedbala, W. G., and Stott, D. I. (1998) A comparison of three methods for production of human hybridomas secreting autoantibodies, *Hybridoma* 17, 299-304.
7. Baselga, J., Tripathy, D., Mendelsohn, J., Baughman, S., Benz, C. C., Dantis, L., Sklarin, N. T., Seidman, A. D., Hudis, C. A., Moore, J., Rosen, P. P., Twaddell, T., Henderson, I. C., and Norton, L. (1996) Phase II study of weekly intravenous recombinant humanized anti-p185HER2 monoclonal antibody in patients with HER2/neu-overexpressing metastatic breast cancer, *J Clin Oncol* 14, 737-744.
8. Eigenbrot, C., Gonzalez, T., Mayeda, J., Carter, P., Werther, W., Hotaling, T., Fox, J., and Kessler, J. (1994) X-ray structures of fragments from binding and nonbinding versions of a humanized anti-CD 18 antibody: structural indications of the key role of VH residues 59 to 65, *Proteins* 18, 49-62.
9. Mian, I. S., Bradwell, A. R., and Olson, A. J. (1991) Structure, function and properties of antibody binding sites, *J Mol Biol* 217, 133-151.
10. Abhinandan, K. R., and Martin, A. C. (2007) Analyzing the "degree of humanness" of antibody sequences, *J Mol Biol* 369, 852-862.
11. Chothia, C., and Lesk, A. M. (1987) Canonical structures for the hypervariable regions of immunoglobulins, *J Mol Biol* 196, 901-917.
12. Chothia, C., Lesk, A. M., Gherardi, E., Tomlinson, I. M., Walter, G., Marks, J. D., Llewelyn, M. B., and Winter, G. (1992) Structural repertoire of the human VH segments, *J Mol Biol* 227, 799-817.
13. Chothia, C., Lesk, A. M., Tramontano, A., Levitt, M., Smith-Gill, S. J., Air, G., Sheriff, S., Padlan, E. A., Davies, D., Tulip, W. R., and et al. (1989) Conformations of immunoglobulin hypervariable regions, *Nature* 342, 877-883.
14. Tramontano, A., Chothia, C., and Lesk, A. M. (1990) Framework residue 71 is a major determinant of the position and conformation of the second hypervariable region in the VH domains of immunoglobulins, *J Mol Biol* 215, 175-182.
15. E. A. Kabat, T. T. W., H. M. Perry, K. S. Gottesman, Foeller. (1991) Sequences of Proteins of Immunological Interest, *U.S. Public Health Service, National Institutes of Health, Washington, D.C.*
16. Almagro, J. C., and Fransson, J. (2008) Humanization of antibodies, *Front Biosci* 13, 1619-1633.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

We claim:

1. A method of producing a humanized antibody or an antigen binding fragment thereof for a non-human antibody to an antigen, comprising:
   (1) constructing a heavy chain variable domain (VH) framework (FR) library comprising nucleic acids encoding a diversity of VHs, each of the VHs comprising FR1, FR2, FR3 and FR4 independently selected from corresponding FRs of a first number of homologous human germline VHs, and corresponding complementarity determining regions (CDRs) of the VH of the non-human antibody;
   (2) constructing a light chain variable domain (VL) FR library comprising nucleic acids encoding a diversity of VLs, each of the VLs comprising FR1, FR2, FR3 and FR4 independently selected from corresponding FRs of a second number of homologous human germline VLs, and corresponding CDRs of the VL of the non-human antibody;
   (3) constructing a framework-assembly library comprising nucleic acids encoding a diversity of Fabs or fragments thereof, each of the Fabs or the fragments thereof comprising a VH encoded by a nucleic acid in the VH FR library and a VL encoded by a nucleic acid in the VL FR library;
   (4) expressing the framework-assembly library in host cells;
   (5) identifying from the expressed framework-assembly library an Fab or a fragment thereof that binds to the antigen;
   (6) identifying the VH and VL in the identified Fab or the fragment thereof as a humanized VH and a humanized VL, respectively, for the humanized antibody or the antigen binding fragment thereof; and
   (7) producing the humanized antibody or the antigen binding fragment thereof comprising the identified humanized VH and the humanized VL,
   wherein the sequences of FR1, FR2, FR3, and FR4 in the VH FR library and VL FR library are natural human germline sequences.

2. The method of claim 1, wherein the framework-assembly library is expressed and the Fab or the fragment thereof is identified using phage-display.

3. The method of claim 1, wherein the host cells are bacterial cells.

4. The method of claim 1, wherein more than one Fab or fragments thereof that bind to the antigen are identified, and the method further comprises measuring expression level of each of the more than one Fabs or fragments thereof in an expression cell, and identifying the VH and VL within the Fab or fragment thereof that has the highest expression level as the humanized VH and the humanized VL, respectively.

5. The method of claim 4, wherein the expression level is measured using a Fast Screen for Expression, Biophysical-properties and Affinity system.

6. The method of claim 1, wherein more than one Fab or fragments thereof that bind to the antigen are identified, and the method further comprises measuring expression level of each of the more than one Fabs or fragments thereof in an expression cell, measuring the binding affinity of each of the more than one Fabs or fragments therein to the antigen, and identifying the VH and VL within the Fab or fragment thereof that has a high expression level and strong binding affinity as the humanized VH and the humanized VL, respectively.

7. The method of claim 1, wherein the non-human antibody is a rodent antibody.

8. The method of claim 1, wherein each of the CDRs of the homologous human germline VHs has the same length as each of the corresponding CDRs in the VH of the non-human antibody, each of the CDRs of the homologous human germline VLs has the same length as each of the corresponding CDRs in the VL of the non-human antibody, and each of the homologous human germline VHs and VLs does not contain a proline, a cysteine or a N-glycosylation site.

9. The method of claim 1, wherein each of the homologous human germline VHs has at least about 60% sequence identity to the VH amino acid sequence of the non-human antibody, and each of the homologous human germline VLs has at least about 70% sequence identity to the VL amino acid sequence of the non-human antibody.

10. The method of claim 1, wherein the first number and the second number are same or different.

11. The method of claim 1, wherein the diversity of the VH FR library and the diversity of the VL FR library are same or different.

12. The method of claim 1, wherein the diversity of the framework assembly library is less than 10,000.

* * * * *